United States Patent [19]

Andrews et al.

[11] Patent Number: 5,543,406
[45] Date of Patent: Aug. 6, 1996

[54] INHIBITORS OF 5-α-TESTOSTERONE REDUCTASE

[75] Inventors: Robert C. Andrews, Durham; Cynthia M. Cribbs, Raleigh; Stephen V. Frye, Durham; Curt D. Haffner, Cary; Patrick R. Maloney, Durham, all of N.C.

[73] Assignee: Glaxo Wellcome, Inc., Research Triangle Park, N.C.

[21] Appl. No.: 244,875

[22] PCT Filed: Dec. 18, 1992

[86] PCT No.: PCT/US92/11109

§ 371 Date: Aug. 15, 1994

§ 102(e) Date: Aug. 15, 1994

[87] PCT Pub. No.: WO/9313124

PCT Pub. Date: Jul. 8, 1993

Related U.S. Application Data

[63] Continuation-in-part of Ser. No. 31,381, Dec. 11, 1992, abandoned, which is a continuation-in-part of Ser. No. 930,101, Aug. 13, 1992, abandoned, which is a continuation-in-part of Ser. No. 905,262, Jun. 26, 1992, abandoned, which is a continuation-in-part of Ser. No. 812,257, Dec. 20, 1991, abandoned.

[51] Int. Cl.⁶ .................. A61K 31/40; A61K 31/435; A61K 31/55
[52] U.S. Cl. .................. 514/213; 514/228.2; 514/232.8; 514/253; 514/280; 514/284; 514/410; 540/572; 546/42; 546/61; 548/418; 548/420
[58] Field of Search .................. 540/572; 546/42.61; 548/418, 420; 514/213, 280, 284, 420, 228.2, 232.8, 253

[56] References Cited

U.S. PATENT DOCUMENTS

| | | | |
|---|---|---|---|
| 4,191,759 | 3/1980 | Johnston et al. | 896/119 |
| 4,361,578 | 11/1982 | Alig et al. | 321/954 |
| 4,377,584 | 3/1983 | Rasmusson et al. | 424/258 |
| 4,882,319 | 11/1989 | Holt et al. | 290/56 |
| 4,888,336 | 12/1989 | Holt et al. | 514/278 |
| 4,937,237 | 6/1990 | Holt et al. | 290/57 |
| 5,017,568 | 5/1991 | Holt et al. | 514/173 |
| 5,061,801 | 10/1991 | Williams et al. | 586/922 |
| 5,061,802 | 10/1991 | Steinberg et al. | 541/250 |
| 5,061,803 | 10/1991 | Williams et al. | 587/299 |
| 5,098,908 | 3/1992 | Steinberg et al. | 540/966 |
| 5,110,939 | 5/1992 | Holt et al. | 419/563 |
| 5,302,589 | 4/1994 | Frye et al. | 514/210 |
| 5,438,061 | 8/1995 | Bergman et al. | 514/284 |

FOREIGN PATENT DOCUMENTS

| | | |
|---|---|---|
| 004949A1 | 4/1979 | European Pat. Off. |
| 314199A1 | 2/1985 | European Pat. Off. |

(List continued on next page.)

OTHER PUBLICATIONS

McGinley, et al., *New England Journal of Medicine*, 300, 1979, pp. 1233–1237.

(List continued on next page.)

*Primary Examiner*—Philip I. Datlow
*Attorney, Agent, or Firm*—Charles E. Dadswell; Robert H. Brink

[57] ABSTRACT

The present invention relates to certain substituted 17β-substituted carbonyl-6-azaandrost-4-en-3-ones of formula (I), especially those of formula (IG)

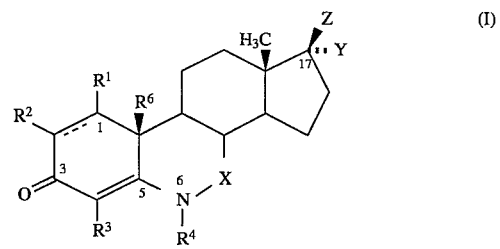

(I)

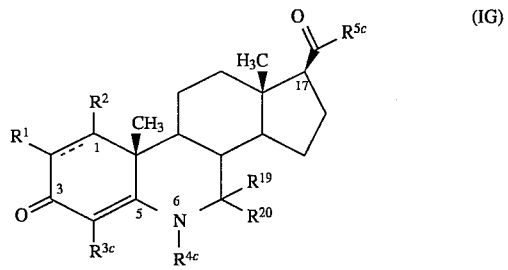

(IG)

wherein
$R^1$ and $R^2$ are
  i) independently hydrogen or lower alkyl and the bond between the carbons bearing $R^1$ and $R^2$ is a single or a double bond, or
  ii) taken together are a —$CH_2$— group to form a cyclopropane ring, and the bond between the carbons bearing $R^1$ and $R^2$ is a single bond;

$R^{3c}$ is hydrogen;
$R^{4c}$ is hydrogen, lower alkyl, lower cycloalkyl, lower alkenyl, alkanoyl of 2–6 carbons, —$(CH_2)_m CO_2 R^{16}$, —$(CH_2)_m Ar^a$, —$(CH_2)_n' CONR^{17} R^{18}$, —$(CH_2)_n' NR^{17} R^{18}$ or —$(CH_2)_n' OR^{16}$, wherein $R^{16}$ is hydrogen, lower alkyl or lower alkenyl; $R^{17}$ and $R^{18}$ are independently hydrogen, lower alkyl lower cycloalkyl or lower alkenyl; $Ar^a$ is an aromatic group of 6 to 12 carbons; n' is 0 or an integer from 1 to 5; m is an integer from 1 to 5;

$R^{19}$ and $R^{20}$ are independently hydrogen or lower alkyl, or taken together $R^{19}$ and $R^{20}$ form a carbonyl group (=O);

$R^{5c}$ is lower alkyl, lower alkenyl, lower cycloalkyl, lower alkoxy, or $NR^{21} R^{22}$, wherein $R^{21}$ and $R^{22}$ are independently hydrogen, lower alkyl or lower alkenyl;

and pharmaceutically acceptable salts thereof, their preparation, medical use and pharmaceutical formulations.

12 Claims, No Drawings

FOREIGN PATENT DOCUMENTS

| | | |
|---|---|---|
| 155096A2 | 2/1985 | European Pat. Off. . |
| 200859A1 | 2/1986 | European Pat. Off. . |
| 271220A1 | 11/1987 | European Pat. Off. . |
| 271219A1 | 11/1987 | European Pat. Off. . |
| 277002A2 | 1/1988 | European Pat. Off. . |
| 285383A2 | 3/1988 | European Pat. Off. . |
| 414491A2 | 8/1990 | European Pat. Off. . |
| 414490A2 | 8/1990 | European Pat. Off. . |
| 428366A2 | 11/1990 | European Pat. Off. . |
| 435321A2 | 12/1990 | European Pat. Off. . |
| 462664A2 | 6/1991 | European Pat. Off. . |
| 462662A2 | 6/1991 | European Pat. Off. . |
| 462661A1 | 6/1991 | European Pat. Off. . |
| 462668A2 | 6/1991 | European Pat. Off. . |
| 469547A2 | 7/1991 | European Pat. Off. . |
| 469548A2 | 7/1991 | European Pat. Off. . |
| 473226A2 | 8/1991 | European Pat. Off. . |
| 473225A2 | 8/1991 | European Pat. Off. . |
| 478066A2 | 9/1991 | European Pat. Off. . |
| 484094A2 | 10/1991 | European Pat. Off. . |
| 484094A2 | 10/1991 | European Pat. Off. . |
| 462665A2 | 6/1992 | European Pat. Off. . |
| WO93/13124 | 7/1983 | WIPO . |
| WO91/12261 | 8/1991 | WIPO . |

OTHER PUBLICATIONS

Hsia, et al., *J. Invest. Derm.*, 62, 1973, p. 224.
Robaire, et al., *J. Steroid Biochem.*, 8, 1977, pp. 307–310.
Petrow, et al., *Steroids*, 38, 1981, p. 121.
Liang, et al., *J. Steroid Biochem*, 19 1983, pp. 385–390.
Holt, et al., *J. Med. Chem*, 33, 1990, 937–942, "Steroidal A Ring Aryl Carboxylic Acids: A New Class of Steroid 5α–Reductase Inhibitors".
Stoner, et al., *J. Steroid Biochem. Molec. Biol.*, vol. 37, 1990, pp. 375–378.
Brooks, et al., *Steroids*, 47, 186, p. 1, "5α–Reductase Inhibitory and Anti–Androgenic Activities of Some 4–Azasteroids in the Rat".
Velthuysen, et al., *Tetrahedron Letters*, 27, 1966, 3081–3086, "Synthesis of (±)–N–Methyl–6–aza–8(14)–Dehydro–19–Nor–Testosterone".
Speckamp, et al., *Tetrahedron*, 24, 1968, 5893–5898, "The Synthesis of N–Methyl–6–Aza–8(14)–Dehydro–19–Nor–Testosterone".

Kutney, et al, *Canadian J. of Chem.*, 41, 1963, 613–619, "Synthesis of 6–Aza Steroids: A Novel Class of Azaandrostane Analogues".
Sampson, et al. *Biochimica et Biophysica Acta*, 960, 1988, 268–274, "The Effects of 6–Azacholest–4–en–3β–ol–7–one, an Inhibitor of Cholesterol 7α–Hydroxylase, on Cholesterol Metabolism and Bile Acid Synthesis in Primary Cultures of Rat Hepatocytes".
Kutney, et al., *Tetrahedron*, 24, 1968, 845–857, "Synthesis of Ring Oxygenated 6–Aza Steroids".
Brown, et al., *J. Chem. Soc.*, 1987, 595–599, "The Synthesis of Some Cholesterol Derivatives as Probes for Mechanisms of Cholesterol Metabolism".
Jacobs, et al, 1960, 4033–4039, "The Introduction of Oxygen and Bitrogen into the B Ring of the Steroid Nucleus".
Speckamp, et al., *Tetrahedron*, 24, 1968, 5881–5891, "Synthesis of N–Methyl and N–Ethyl–6–Aza–8(14)–Dehydroestrone Methyl Ether".
Hugl, et al., *Tetrahedron*, v. 29, 173, 759–767, "Umsetzungen Von $\Delta^5$–Steroidolefinen Mit $Pb(OAc)_{4-n}(N_3)_n$".
Kutney, et al., *Chem and Ind*, 1961, 1713–1714, "Synthesis of 6–Aza–Steroids: A Novel Class of Steroidal Hormones".
Rasmusson, et al., *J. Med. Chem.*, 29, 1986, pp. 2298–2315, "Steroids: Structure–Activity Relationships for Inhibition of 5α–Reductase and Androgen Receptor Binding".
Mathes, et al.,H. Lettré, 703, 1967, 147–151, "Verbesserung der darstellung von 6–Aza–Steroiden".
Rasmusson, et al., *J. of Med. Chem.*, 27, 184, pp. 1690–1701, "Azasteroids as Inhibitors of Rat Prostatic 5α–Reductase".
Imperato, et al., *TIG*, 1986, 130–133, "Inherited 5α–Reductase Deficiency in Man".
Jones, et al., *British J. of Urology*, 66, 1990, pp. 506–508, "Origin and Structure of Benign Prostatic Hyperplasia".
Bhattacharya, et al, *Synthetic Communications*, 30(17), 1990, 2683–2690, "Acylimidazolides as Versatile Synthetic Intermediates for the Preparation of Sterically Congested Amides and Ketones: A Practical Synthesis of Proscar®".
Dave, et al., *Canadian J. of Chemistry*, 58(23), 1980, 2666–2678, "Resolution of Conflicting Migratory Reports in Ring Expansion of 3–keto Steroids of Oxygen and Nitrogen".

INHIBITORS OF 5-α-TESTOSTERONE REDUCTASE

The present application is the National Stage of Application PCT US 92/11109 filed Dec. 18, 1992 which is a Continuation-In-Part of application Ser. No. 08/031,381 now abandoned, filed Dec. 11, 1992, which is a Continuation-In-Part of application Ser. No. 07/930,101 now abandoned, filed Aug. 13, 1992 which is a Continuation-In-Part of application Ser. No. 07/905,262 now abandoned, filed Jun. 26, 1992 which in turn is a Continuation-In-Part of application Ser. No. 07/812,257 filed Dec. 20, 1991, now abandoned.

The present invention relates to certain substituted 17β-substituted-6-azaandrost-4-en-3-ones and their use as 5α-testosterone reductase inhibitors.

BACKGROUND OF THE INVENTION

Androgens are responsible for many physiological functions in both males and females. Androgen action is mediated by specific intracellular hormone receptors expressed in androgen responsive cells. Testosterone, the major circulating androgen, is secreted by Leydig cells of the testes under the stimulation of pituitary-derived luteinizing hormone (LH). However, reduction of the 4,5 double bond of testosterone to dihydrotestosterone (DHT) is required in some target tissues, such as prostate and skin, for androgen action. Steroid 5α-reductase in target tissues catalyzes conversion of testosterone to DHT in an NADPH dependent fashion as shown in Scheme A.

SCHEME A

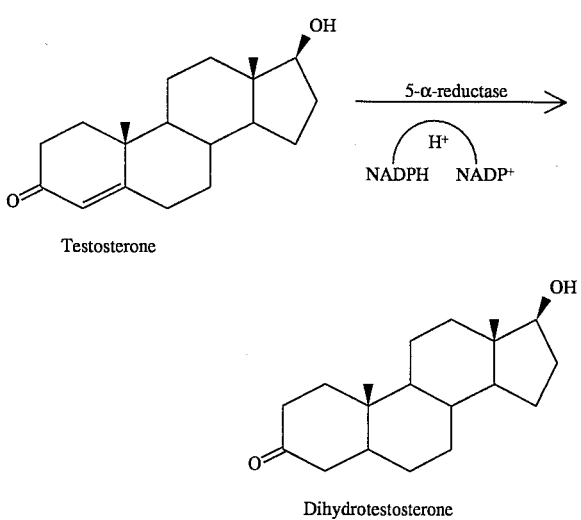

Testosterone

Dihydrotestosterone

The requirement for DHT to act as an agonist in these target tissues has been highlighted by studies of steroid 5α-reductase deficient individuals who have vestigial prostate glands and do not suffer from acne vulgaris or male pattern baldness (see McGinley, J., et al, *J. Steroid Biochem.*, 11, 637–648, (1979)). Thus, inhibition of the conversion of testosterone to DHT in these target tissues is anticipated to be useful in the treatment of a variety of androgen responsive diseases, e.g., benign prostatic hypertrophy, prostate cancer, acne, male pattern baldness and hirsutism.

Because of their valuable therapeutic potential, testosterone 5α-reductase inhibitors [hereinafter "5α-reductase inhibitors"] have been the subject of active research worldwide. For example, see: Hsia, S. and Voight, W., *J. Invest. Derm.*, 62, 224 (1973); Robaire, B., et al., *J. Steroid Biochem.*, 8, 307 (1977); Petrow, V., et al., *Steroids*, 38, 121 (1981); Liang, T., et al., *J. Steroid Biochem.*, 19, 395 (1983); Holt, D., *J. Med. Chem.*, 33, 937 (1990); U.S. Pat. Nos. 4,377,584 and 5,017,568. Two particularly promising 5α-reductase inhibitors currently in clinical trials are MK-906 (Merck) and SKF-105657 (SmithKline Beecham), shown in Scheme B.

SCHEME B

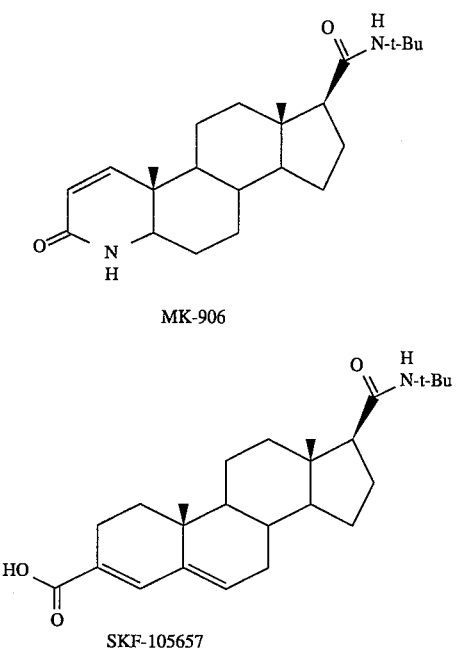

SUMMARY OF THE INVENTION

One aspect of the present invention are the compounds of formula (I),

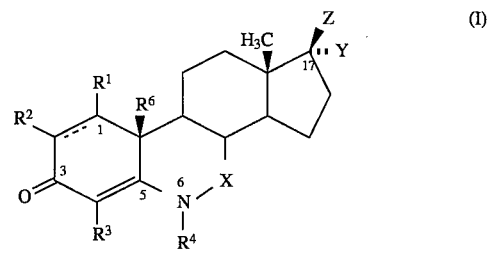

wherein $R^1$ and $R^2$ are,
  i) independently hydrogen or lower alkyl and the bond between the carbons bearing $R^1$ and $R^2$ is a single or a double bond, or
  ii) taken together are a —CH$_2$— group to form a cyclopropane ring, and the bond between the carbons bearing $R^1$ and $R^2$ is a single bond;

$R^3$ is hydrogen, -Alk$^1$-H optionally substituted with one or more halogen atoms, lower cycloalkyl, lower cycloalkyl-lower alkyl, halogen, -(Alk$^1$)$_n$-CO$_2$H, -(Alk$^1$)$_n$-CO$_2$R$^7$, -(Alk$^1$)$_n$-Ar$^1$, -(Alk$^1$)$_n$-CONR$^8$R$^9$, -(Alk$_1$)$_n$-NR$^8$R$^9$, -(Alk$^1$)$_n$-S(O)$_r$R$^7$, -(Alk$^1$)$_n$-CN, -(Alk$^1$)-OH or -(Alk$^1$)$_n$-OR$^7$; wherein Alk$^1$ is lower alkylene, lower alkenylene or lower alkynylene;

n is 0 or 1;
r is 0, 1 or 2;
$R^7$ is -$Alk^1$-H, -$(Alk^1)_n$-$Ar^1$ or lower cycloalkyl;
$R^8$ and $R^9$ are independently hydrogen, -$Alk^1$-H or lower cycloalkyl;
$Ar^1$ is an aromatic group of 6 to 14 carbons;
$R^4$ is hydrogen, -$Alk^1$-H, lower cycloalkyl, lower cycloalkyl-lower alkyl, -$(Alk^1)_n$-$S(O)_r R^7$, -$(Alk^1)_n$-phthalimidyl, -$(Alk^1)$-$CO_2H$, -$(Alk^1)_n$-$CO_2R^7$, -$(Alk^1)_n$-$Ar^1$, -$(Alk^1)_n$-$CONR^8R^9$, -$(Alk^1)_n$-$NR^8R^9$, -$(Alk^1)_n$-OH or -$(Alk^1)_n$-$OR^7$;

X is,

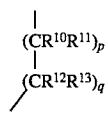

wherein
$R^{10}$, $R^{11}$, $R^{12}$ and $R^{13}$ are independently hydrogen or lower alkyl,
p and q are independently either 0 or 1;
Y is hydrogen;
Z is -$(Alk^2)_n$-$COR^5$, -$(Alk^2)_n$-$CO_2R^5$, -$(Alk^2)_n$-CO-thiopyridinyl or -$(Alk^2)_n$-$CONR^{14}R^{15}$, wherein
$Alk^2$ is $(C_{1-12})$ alkylene, $(C_{2-12})$ alkenylene or $(C_{2-12})$ alkynylene;
$R^5$ is hydrogen, -$Alk^1$-H, lower cycloalkyl or adamantyl;
$R^{14}$ and $R^{15}$ are,
a) independently, hydrogen, -$Alk^2$-H, lower cycloalkyl, lower alkoxy, adamantyl, -$Ar^1$, benzyl, diphenylmethyl, triphenylmethyl or -$(Alk^1)_n$-norbornyl; or
b) taken together with the linking nitrogen to form a 4 to 8 atom heterocyclic group

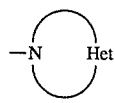

wherein;
Het represents —O—, —$CH_2$—, —$S(O)_r$—, —NH— or —N(-$Alk^1$-H)—; optionally substituted with one or more lower alkyl groups;
$R^6$ is hydrogen or methyl;
and pharmaceutically acceptable salts thereof.

A second aspect of the invention is a method of inhibiting testosterone-5α-reductase comprising contacting testosterone-5α-reductase with a compound of formula (I).

Another aspect of the invention is a method of treatment of androgen responsive or mediated disease comprising administering an effective amount of a compound of formula (I) to a patient in need of such treatment.

A further aspect comprises pharmaceutical formulations containing a compound of formula (I) as an active ingredient. Novel chemical intermediates used in the synthesis, as taught herein, of the compounds of formula (I) are also within the scope of the present invention.

DETAILED DESCRIPTION OF THE INVENTION

Compounds

As used herein the term "lower" in reference to alkyl and alkoxy means 1-6 carbons, straight or branched chain, i.e., methyl, ethyl, propyl, butyl, pentyl and hexyl; and methoxy, ethoxy, propoxy, butoxy, pentoxy and hexoxy respectively. In reference to alkenyl or alkynyl "lower" means 2-6 carbons, straight or branched chain i.e., ethenyl, propenyl, butenyl, pentenyl and hexenyl; and ethynyl, propynyl, butynyl, pentynyl and hexynyl respectively. In reference to cycloalkyl "lower" means 3-6 carbons, i.e., cyclopropyl, cyclobutyl, cyclopentyl and cyclohexyl. The term "lower cycloalkyl-lower alkyl" means a lower alkyl bearing a lower cycloalkyl, e.g., cyclopropylmethyl which may also be named methylene-cyclopropyl.

The term "alkanoyl of 2-6 carbons" refers to alkyl, straight or branched, carboxylic acid groups with a total of 2-6 carbons attached to the structure of formula (I) at a carbon of the alkyl portion of the group, e.g., —$CH_2COOH$, —$(CH_2)_2COOH$, —$(CH_2)_3COOH$, —$(CH_2)_4COOH$ and —$(CH_2)_5COOH$.

The term "halogen" means fluoro, chloro, bromo and iodo. Halogenated alkyl groups are preferably fluorinated e.g. trifluoromethyl.

The term "aromatic group" means homocyclic aromatic groups having 6 to 14 carbons and includes, but is not limited to, phenyl, napthyl and anthracyl.

Where $R^{14}$ and $R^{15}$ when taken together with the linking nitrogen form a 4 to 8 atom heterocyclic group, such groups which may be formed include, but are not limited to, pyrrolidinyl, imidazolidinyl, pyrazolidinyl, piperidinyl, piperazinyl, morpholinyl or thiomorpholinyl each optionally substituted with one or more lower alkyl groups.

In one preferred group of compounds of formula (I) Z is —$COR^5$, —$CO_2R^5$, —CO-thiopyridinyl, —$CONR^{14}R^{15}$ or —CH═$CHCOR^5$, especially —COOH, —$COOCH_3$, adamantylcarbamoyl, t-butylcarbamoyl, oxomethylbutyl, methoxymethylcarbamoyl, dimethycarbamoyl, diethylcarbamoyl, di-i-propylcarbamoyl, di-t-butylcarbamoyl, piperazinocarbamoyl, morpholinocarbamoyl, 2-methylpropylcarbamoyl, pyridinylthiocarbonyl, diphenylmethylcarbamoyl, triphenylmethylcarbamoyl, diphenylcarbamoyl, naphthylcarbamoyl, anthracylcarbamoyl, carboadamantyloxy, acrylyldiethylamide, exonorbornylmethylcarbamoyl, endonorbornylcarbamoyl, thiomorpholinocarbamoyl or benzylcarbamoyl.

In a further preferred group of compounds of formula (I) $R^3$ is hydrogen, 'lower alkyl, trifluoromethyl, halogen, -(lower alkyl)$_n$-$NR^8R^9$, -(lower alkyl)$_n$-CN, especially hydrogen, methyl, ethyl, cyano, iodo, bromo, chloro or dimethylaminomethyl.

In a further preferred group of compounds of formula (I) $R^4$ is hydrogen, lower alkyl, lower alkyl, lower cycloalkyl, lower cycloalkyl-lower alkyl, -(lower alkyl)$_n$- phthalimidyl, -(lower alkyl)-$CO_2H$, -(lower alkyl)$_n$-$CO_2R^7$, -(lower alkyl)$_n$-$Ar^1$ (e.g. benzyl), -(lower alkyl)$_n$-OH or -(lower alkyl)$_n$-$OR^7$; wherein $R^7$ is lower alkyl; and $Ar^1$ is an aromatic group of 6 to 14 carbon atoms (e.g. phenyl, naphthyl, anthracyl), especially hydrogen, methyl, ethyl, propyl, i-propyl, butyl, t-butyl, t-butyl, hexyl, 3-hydroxypropyl, propenyl, methylene-cyclopropyl, benzyl, 2-methoxyethyl, 2-acetic acid, 3-propanoic acid, 4-butanoic acid, 5-pentanoic acid, 6-hexanoic acid, methyl-5-pentanoate, ethyl-6-hexanoate, 3-phthalimidylpropyl or 4-phthalimidylbutyl.

In a further preferred group of compounds of formula (I) $Alk^2$ is $Alk^1$. Preferably $Alk^1$ is $C_{1-4}$alkylene or $C_{1-4}$alkenylene, especially —$CH_2$—, —$CH_2CH_2$— or —CH═CH—.

Particular compounds of formula (I) are those wherein $R^1$ and $R^2$ are, i) independently hydrogen or lower alkyl and the bond between the carbons bearing $R^1$ and $R^2$ is a single or a double bond, or ii) taken together are a —$CH_2$— group to form a cyclopropane ring, and the bond between the carbons bearing $R^1$ and $R^2$ is a single bond;

$R^3$ is hydrogen, -$Alk^1$-H, perfluorinated lower alkyl, lower cycloalkyl, lower cycloalkyl-lower alkyl, halogen, -$(Alk^1)_n$-$NR^8R^9$ or -$(Alk^1)_n$-CN; wherein $Alk^1$ is lower alkylene or lower alkenylene;

n is 0 or 1; and $R^8$ and $R^9$ are independently hydrogen, -$Alk^1$-H or lower cycloalkyl;

$R^4$ is hydrogen, -$Alk^1$H, lower cycloalkyl, lower cycloalkyl-lower alkyl, -$(Alk^1)_n$-S(O)$_r$-S(O)$_rR^7$, -$(Alk^1)_n$-phthalimidyl, -$(Alk^1)$-$CO_2H$, -$(Alk^1)_n$-$CO_2R^7$, -$(Alk^1)_n$-$Ar^1$, -$(Alk^1)_n$-OH or -$(Alk^1)_n$-$OR^7$; wherein r is 0, 1 of 2;

$R^7$ is -$Alk^1$-H, -$(Alk^1)_n$-$Ar^1$ or lower cycloalkyl; and $Ar^1$ is an aromatic group of 6 to 14 carbons;

X is,

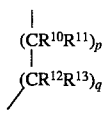

wherein $R^{10}$, $R^{11}$, $R^{12}$ and $R^{13}$ are independently hydrogen or lower alkyl, p and q are independently either 0 or 1;

Y is hydrogen;

Z is -$(Alk^2)_n$-$COR^5$, -$(Alk^2)_n$-$CO_2R^5$, -$(Alk^2)_n$-CO-thiopyridinyl or $(Alk^2)_n$-$CONR^{14}R^{15}$, wherein $Alk^2$ is ($C_{1-12}$) alkylene, ($C_{2-12}$) alkenylene or ($C_{2-12}$) alkynylene;

$R^5$ is hydrogen, $Alk^1$, lower cycloalkyl or adamantyl;

$R^{14}$ and $R^{15}$ are, a) independently, hydrogen, -$Alk^2$-H, lower cycloalkyl, lower alkoxy, adamantyl, -$Ar^1$, benzyl, diphenylmethyl, triphenylmethyl or -$(Alk^1)_n$-norbornyl; or b) taken together with the linking nitrogen to form a 5 to 7 atom heterocyclic group

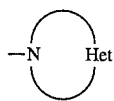

wherein;

Het represents —O—, —$CH_2$—, —S(O)$_r$—, —NH— or —N(-$Alk^1$-H)—;

optionally substituted with one or more lower alkyl groups;

$R^6$ is hydrogen or methyl;

and pharmaceutically acceptable salts thereof.

Preferred compounds of formula (I) are those wherein $R^1$ and $R^2$ are, i) hydrogen and the bond between the carbons bearing $R^1$ and $R^2$ is a single or a double bond, or ii) taken together are a —$CH_2$— group to form a cyclopropane ring, and the bond between the carbons bearing $R^1$ and $R^2$ is a single bond;

$R^3$ is hydrogen, lower alkyl, trifluoromethyl, halogen, -(lower alkyl)$_n$-$NR^8R^9$, or -(lower alkyl)$_n$-CN; wherein n is 0 or 1;

$R^8$ and $R^9$ are independently hydrogen or lower alkyl;

$R^4$ is hydrogen, lower alkyl, lower alkyl, lower cycloalkyl, lower cycloalkyl-lower alkyl, -(lower alkyl)$_n$-phthalimidyl, -(lower alkyl)-$CO_2H$, -(lower alkyl)$_n$-$CO_2R^7$, -(lower alkyl)$_n$-$Ar^1$ (e.g. benzyl) -(lower alkyl)$_n$-OH or -(lower alkyl)$_n$-$OR^7$. wherein $R^7$ is lower alkyl; and $Ar^1$ is an aromatic group of 6 to 14 carbon atoms (e.g. phenyl, naphthyl, anthacyl);

X is, —$CH_2$— or —$CH_2CH_2$—;

Y is hydrogen;

Z is -$(Alk^2)_n$-$COR^5$, -$(Alk^2)_n$-$CO_2R^5$, -$(Alk^2)_n$-CO-thiopyridinyl or $(Alk^2)_n$-$CONR^{14}R^{15}$, wherein $Alk^2$ is ($C_{1-12}$) alkylene or ($C_{2-12}$) alkenylene;

$R^5$ is hydrogen, lower alkyl or adamantyl;

$R^{14}$ and $R^{15}$ are, a) independently, hydrogen, ($C_{1-12}$)alkyl, lower alkoxy, adamantyl, $Ar^1$, benzyl, diphenylmethyl, triphenylmethyl or -(lower alkyl)$_n$-norbornyl; or b) taken together with the linking nitrogen to form a 5 to 7 atom heterocyclic group

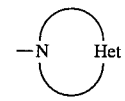

wherein;

Het represents —O—, —S—, —NH— or —N(lower alkyl)-;

optionally substituted with one or more lower alkyl groups (e.g. morpholino, thiomorpholino, piperazino);

$R^6$ is hydrogen or methyl;

and pharmaceutically acceptable salts thereof.

Particular groups of compounds of formula (I) are the compounds of formulas (IA), (IB), (IC) and (ID)

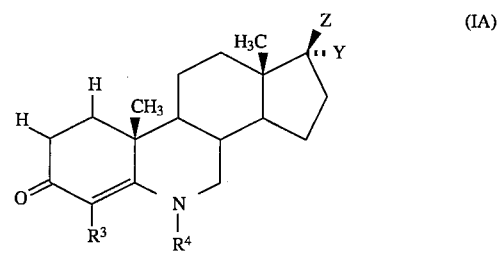

(IA)

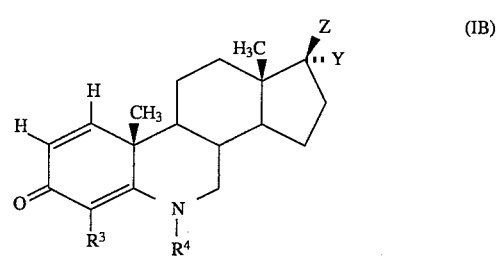

(IB)

-continued

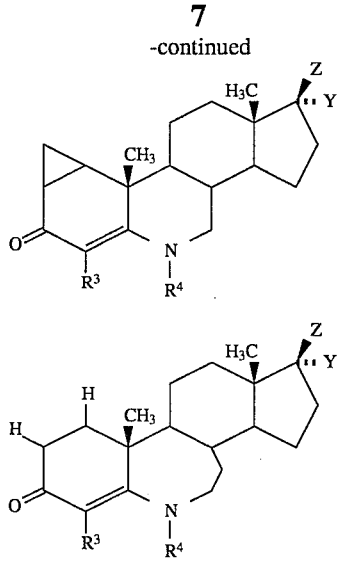

The compounds of formula (I) include the compounds of formula (IE)

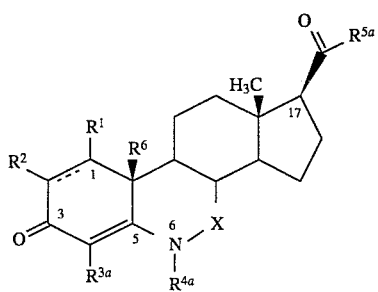

wherein
$R^1$, $R^2$, $R^6$, $R^7$–$R^{13}$, p, q, Ar and X are as defined for formula (I);

$R^{3a}$ is hydrogen, lower alkyl, lower cycloalkyl, lower cycloalkyl-lower alkyl, lower alkenyl, lower alkynyl, alkanoyl of 2-6 carbons, halogen, —$(CH_2)_{n'}$-$CO_2R^7$, —$(CH_2)_{n'}$-Ar, —$(CH_2)_{n'}$-$CONR^8R^9$, —$(CH_2)_{n'}$—$NR^8R^9$, —$(CH_2)_{n'}$—CN or —$(CH_2)_{n'}$—$OR^7$ wherein n' is 0 or an integer from 1 to 5;

$R^{4a}$ is hydrogen, lower alkyl, lower cycloalkyl, lower cycloalkyl-lower alkyl, cycloalkyl, lower alkenyl, lower alkynyl, $(CH_2)_m$phthalimidyl, —$(CH_2)_m CO_2R^7$, —$(CH_2)_{n'}$Ar, —$(CH_2)_m CONR^8R^9$, —$(CH_2)_m NR^8R^9$ or —$(CH_2)_n OR^7$, wherein
m is an integer from 1 to 5;

$R^{5a}$ is lower alkyl, lower alkenyl, lower cycloalkyl, lower alkoxy, thiopyridinyl, adamantyl, $NR^{14a}R^{15a}$ or Ar—$NR^{14a}R^{15a}$ wherein
$R^{14a}$ and $R^{15a}$ are
  i) independently, hydrogen or lower alkyl, lower alkenyl, lower alkynyl, lower cycloalkyl, lower alkoxy, adamantyl, aryl, benzyl, diphenylmethyl, norbornyl or
  ii) taken together with the linking nitrogen to form a 4 to 8 atom heterocyclic group

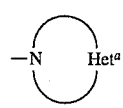

wherein;
$Het^a$ represents O, $CH_2$, NH or N(lower alkyl) optionally substituted with one or more lower alkyl groups;

$R^6$ is hydrogen or methyl;
and pharmaceutically acceptable salts thereof.

The compounds of formula (I) also include the compounds of formula (IF)

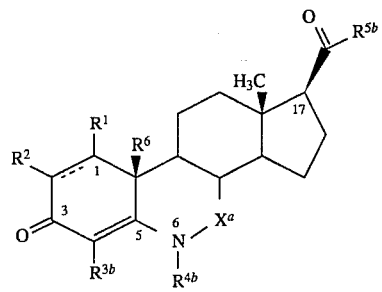

wherein
$R^1$, $R^2$, $R^6$–$R^9$, p, q, Ar are as defined for Formula (I);

$R^{3b}$ is hydrogen, lower alkyl, lower cycloalkyl, lower cycloalkyl-lower alkyl, lower alkenyl, lower alkynyl, alkanoyl of 2-6 carbons, halogen, —$(CH_2)_n CO_2R^7$, —$(CH_2)_n$Ar, —$(CH_2)_n CONR^8R^9$, —$(CH_2)_n NR^8R^9$, —$(CH_2)_n CN$ or —$(CH_2)_n OR^7$ wherein
n' is 0 or an integer from 1 to 5;

$R^{4b}$ is hydrogen, lower alkyl, lower cycloalkyl, lower cycloalkyl-lower alkyl, lower alkenyl, lower alkynyl, $(CH_2)_m$phthalimidyl, —$(CH_2)_n CO_2R^7$, —$(CH_2)_n$Ar, —$(CH_2)_m CONR^8R^9$, —$(CH_2)_n NR^8R^9$ or —$(CH_2)_n OR^7$, wherein
m is an integer from 1 to 5;

$X^a$ is

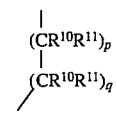

wherein
$R^{10}$ and $R^{11}$ are independently hydrogen or lower alkyl;
$R^{5b}$ is lower alkyl, lower alkenyl, lower cycloalkyl, lower alkoxy, thiopyridinyl, adamantyl, $NR^{14b}R^{15b}$ or Ar—$NR^{14b}R^{15b}$ wherein
$R^{14b}$ and $R^{15b}$ are
  i) independently, hydrogen or lower alkyl, lower alkenyl, lower alkynyl, lower cycloalkyl, lower alkoxy, adamantyl, aryl, benzyl, diphenylmethyl, norbornyl or
  ii) taken together with the linking nitrogen to form a 4 to 8 atom heterocyclic group
$R^6$ is hydrogen or methyl,
and pharmaceutically acceptable salts thereof.

The compounds of formula (I) also include the compounds of formula (IG)

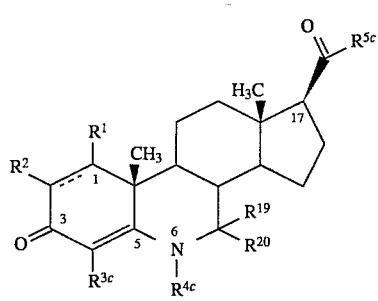

wherein $R^1$ and $R^2$ are as defined for Formula (I);

$R^{3c}$ is hydrogen;

$R^{4c}$ is hydrogen, lower alkyl, lower cycloalkyl, lower alkenyl, alkanoyl of 2–6 carbons, $-(CH_2)_m-CO_2R^{16}$, $-(CH_2)_m-Ar^a$, $-(CH_2)_n'-CONR^{17}R^{18}$, $-(CH_2)_n'-NR^{17}R^{18}$ or $-(CH_2)_n'OR^{16}$, wherein $R^{16}$ is hydrogen, lower alkyl or lower alkenyl;

$R^{17}$ and $R^{18}$ are independently hydrogen, lower alkyl, lower cycloalkyl or lower alkenyl;

$Ar^a$ is an aromatic group of 6 to 12 carbons;

n' is 0 or an integer from 1 to 5;

m is an integer from 1 to 5;

$R^{19}$ and $R^{20}$ are independently hydrogen or lower alkyl, or taken together $R^{19}$ and $R^{20}$ form a carbonyl group(=O);

$R^{5c}$ is lower alkyl, lower alkenyl, lower cycloalkyl, lower alkoxy, or $NR^{21}R^{22}$, wherein $R^{21}$ and $R^{22}$ are independently hydrogen, lower alkyl or lower alkenyl;

and pharmaceutically acceptable salts thereof.

Specific compounds of formula (I) are:

| Compound/Example Number | Compound Name |
|---|---|
| 1. | 17β-N,N-Diethylcarbamoly-6-azaandrost-4-en-3-one |
| 2. | 17β-N,N-Diethylcarbamoly-6-methyl-6-azaandrost-4-en-3-one |
| 3. | 17β-N-t-Butylcarbamoyl-6-azaandrost-4-en-3-one |
| 4. | 17β-(2-Pyridinylthiocarbonyl)-6-azaandrost-4-en-3-one |
| 5. | 17β-(1-Oxo-3-methylbutyl)-6-azaandrost-4-en-3-one |
| 6. | 17β-N,N-Diethylcarbamoyl-6-azaandrost-1,4-dien-3-one |
| 7. | 17β-N,N-Diethylcarbamoyl-6-azaandrost-1α,2α-cyclopropyl-4-en-3-one |
| 8. | 17β-N,N-Diethylcarbamoyl-6-azaandrost-4-chloro-4-en-3-one |
| 9. | 17β-N,N-Diethylcarbamoyl-6-azaandrost-4-bromo-4-en-3-one |
| 10. | 17β-N,N-Diethylcarbamoyl-6-azaandrost-4-iodo-4-en-3-one |
| 11. | 17β-N,N-Diethylcarbamoyl-6-azaandrost-4-methyl-4-en-3-one |
| 12. | 17β-N,N-Diethylcarbamoyl-6-azaandrost-4-ethyl-4-en-3-one |
| 13. | 17β-N,N-Diethylcarbamoyl-6-azaandrost-4-cyano-4-en-3-one |
| 14. | 17β-N,N-Diethylcarbamoyl-6-azaandrost-4-dimethylaminomethylele-4-en-3-one |
| 15. | 17β-N,N-Diethylcarbamoyl-6-(3-hydroxypropyl)-6-azaandrost-4-en-3-one |
| 16. | 17β-N-t-Butylcarbamoyl-6-methyl-6-azaandrost-4-en-3-one |
| 17. | 17β-N,N-Diisopropylcarbamoyl-6-azaandrost-4-en-3-one |
| 18. | 17β-N,N-Diisopropylcarbamoyl-6-methyl-6-azaandrost-4-en-3-one |
| 19. | 17β-N,N-Adamantylcarbamoyl-6-azaandrost-4-en-3-one |
| 20. | 17β-N,N-Adamantylcarbamoyl-6-methyl-6-azaandrost-4-en-3-one |
| 21. | 17β-N-Methoxy-N-methylcarbamoyl-6-azaandrost-4-en-3-one |
| 22. | 17β-N-Piperizinocarbamoyl-6-azaandrost-4-en-3-one |
| 23. | 17β-N-Morpholinocarbamoyl-6-azaandrost-4-en-3-one |
| 24. | 17β-Carbomethoxy-6-azaandrost-4-en-3-one |
| 25. | 17β-Carboxy-6-methyl-6-azaandrost-4-en-3-one |
| 26. | 17β-(1-Oxo-3-methylbutyl)-6-methyl-6-azaandrost-4-en-3-one |
| 27. | 17β-N,N-Diethylcarbamoyl-6-methyl-6-azaandrost-1,4-dien-3-one |
| 28. | 17β-N-t-Butylcarbamoyl-6-azaandrost-1,4-dien-3-one |
| 29. | 17β-N-t-Butylcarbamoyl-6-methyl-6-azaandrost-1,4-dien-3-one |
| 30. | 17β-N-1-Adamantylcarbamoyl-6-azaandrost-1,4-dien-3-one |
| 31. | 17β-N-1-Adamantylcarbamoyl-6-methyl-6-azaandrost-1,4-dien-3-one |
| 32. | 17β-N,N-Diethylcarbamoyl-6-methyl-6-azaandrost-1α,2α-cyclopropyl-4-en-3-one |
| 33. | 17β-N-t-Diethylcarbamoyl-6-azaandrost-1α,2α-cyclopropyl-4-en-3-one |
| 34. | 17β-N-t-Butylcarbamoyl-6-methyl-6-azaandrost-1α,2α,-cyclopropyl-4-en-3-one |
| 35. | 17β-N,N-Diethylcarbamoyl-6-ethyl-6-azaandrost-4-en-3-one |
| 36. | 17β-N,N-Diethylcarbamoyl-6-propyl-6-azaandrost-4-en-3-one |
| 37. | 17β-N,N-Diethylcarbamoyl-6-butyl-6-azaandrost-4-en-3-one |
| 38. | 17β-N,N-Diethylcarbamoyl-6-hexyl-6-azaandrost-4-en-3-one |
| 39. | 17β-N,N-Diethylcarbamoyl-6-isopropyl-6-azaandrost-4-en-3-one |
| 40. | 17β-N,N-Diethylcarbamoyl-6-isobutyl-6-azaandrost-4-en-3-one |
| 41. | 17β-N,N-Diethylcarbamoyl-6-methylene-cyclopropyl-6-azaandrost-4-en-3-one |
| 42 | 17β-N,N-Diethylcarbamoyl-6-allyl-6-azaandrost-4-en-3-one |
| 43. | 17β-N,N-Diethylcarbamoyl-6-benzyl-6-azaandrost-4-en-3-one |
| 44. | 17β-N,N-Diethylcarbamoyl-6-(2-acetic acid)-6-azaandrost-4-en-3-one |
| 45. | 17β-N,N-Diethylcarbamoyl-6-(3-propanoic acid)-6-azaandrost-4-en-3-one |
| 46. | 17β-N,N-Diethylcarbamoyl-6-(methyl-3-propanoate)-6-azaandrost-4-en-3-one |
| 47. | 17β-N,N-Diethylcarbamoyl-6-(4-butanoic acid)-6-azaandrost-4-en-3-one |
| 48. | 17β-N,N-Diethylcarbamoyl-6-(5-pentanoic acid)-6-azaandrost-4-en-3-one |
| 49. | 17β-N,N-Diethylcarbamoyl-6-(methyl-5-pentanoite)-6-azaandrost-4-en-3-one |
| 50. | 17β-N,N-Diethylcarbamoyl-6-(6-hexanoic acid)-6-azaandrost-4-en-3-one |
| 52. | 17β-N,N-Diethylcarbamoyl-6-(ethyl-6-hexanoate)-6-azaandrost-4-en-3-one |
| 52. | 17β-N,N-Diethylcarbamoyl-6-(3-phthalimidylpropyl)-6-azaandrost-4-en-3-one |
| 53. | 17β-N,N-Diethylcarbamoyl-6-(4-phthalimidylpropyl)-6-azaandrost-4-en-3 one |

| Compound/Example Number | Compound Name |
| --- | --- |
| 54. | 17β-N,N-Diethylcarbamoyl-6-(2-methoxyethyl)-6-azaandrost-4-en-3-one |
| 55. | 17β-N-1-Adamantylcarbamoyl-6-azaandrost-4-bromo-4-en-3-one |
| 56. | 17β-N-1-Adamantylcarbamoyl-6-azaandrost-4-methyl-4-en-3-one |
| 57. | 17β-N-1-Adamantylcarbamoyl-6-methyl-6-azaandrost-4-methyl-4-en-3-one |
| 58. | 17β-N-Diphenylmethylcarbamoyl-6-azaandrost-4-en-3-one |
| 59 | 17β-N-Diphenylcarbamoyl-6-azaandrost-4-en-3-one |
| 60. | 17β-N-exo-2-Norbornylmethylcarbamoyl-6-azaandrost-4-en-3-one |
| 62. | 17β-N-endo-2-Norbornylcarbamoyl-6-azaandrost-4-en-3-one |
| 62. | 17β-N-Butylcarbamoyl-6-azaandrost-4-methyl-4-en-3-one |
| 63. | 17β-N-Thiomorpholincarbamoyl-6-azaandrost-4-en-3-one |
| 64. | 17β-(1-Oxo-3-methylbutyl)-6-azaandrost-4-methyl-4-en-3-one |
| 65. | 17β-N-Benzylcarbamoyl-6-azaandrost-4-en-3-one |
| 66. | 17β-(1-Oxo-3-methylbutyl)-6-azaandrost-4-bromo-4-en-3-one |
| 67. | 17β-N-1-Anthracylcarbamoyl-6-azaandrost-4-en-3-one |
| 68. | 17β-N,N-Diethylcarbamoyl-6-methyl-6-azaandrost-4-methyl-4-en-3-one |
| 69. | 17β-N-t-Butylcarbamoyl-6-methyl-6-azaandrost-4-methyl-4-en-3-one |
| 70. | 17β-N,N-Diethylcarbamoyl-6-azaandrost-4-fluoro-4-en-3-one |
| 71. | 17β-N-Triphenylmethylcarbamoyl-6-azaandrost-4-en-3-one |
| 72. | 17β-N-1-Naphthylcarbamoyl-6-azaandrost-4-en-3-one |
| 73. | 17β-Carbo-(2-adamantly)-oxy-6-azaandrost-4-en-3-one |
| 74. | 17β-Carbo-(1-adamantyl)-oxy-6-azaandrost-4-en-3-one |
| 75. | 17β-N,N-Diethylcarbamoyl-6-azaandrost-2(α,β)-methyl-4-en-3-one |
| 76. | 17β-1-(E)-Acrylyl(N,N-diethyl)amide-6-azaandrost-4-en-3-one |
| 77. | 17β-N,N-Diethylcarbamoyl-6-aza-B-homoandrost-4-en-3-one |

Some of the substituents of the compound of formula (I) may cause asymmetry about the atoms to which they are attached giving rise to either α or β stereochemical configuration. (For a detailed explanation of stereochemical configuration see March, *J. Advanced Organic Chemistry*, 3rd Ed., ch 4, John Wiley & Sons, New York (1985).) Unless otherwise indicated, either the α and β stereo configurations are intended for the substituents.

The compounds of formula (I) can be used in the form of an acid addition salt derived from inorganic or organic acids. Where the salt of a compound of formula (I) is to be used for a human or veterinary medicinal application the salt must be pharmaceutically acceptable. However, non-pharmaceutically acceptable salts of the compounds of formula (I) may be useful as intermediates in the preparation of a corresponding pharmaceutically acceptable salt. Pharmaceutically acceptable salts include, but are not limited to, salts with inorganic acids such as hydrochloride, sulfate, phosphate, diphosphate, hydrobromide and nitrate salts or salts with an organic acid such as the acetate, malate, maleate, fumarate, tartrate, succinate, citrate, lactate, methanesulfonate, p-toluenesulfonate, palmitoate, salicylate and stearate salts.

Preparation of Compounds

According to one general process (A), the compounds of the present invention may be prepared by the procedure shown in Step 8 of Scheme I, wherein $R^1$–$R^4$, $R^6$, Y and Z are as defined for formula (I) and "JO" is a protected hydroxy group:

SCHEME I

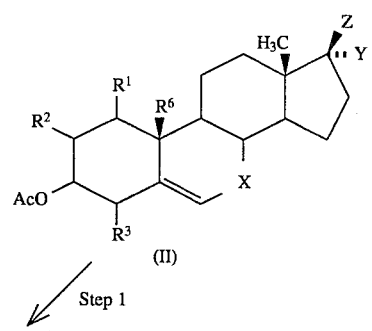

-continued
SCHEME I
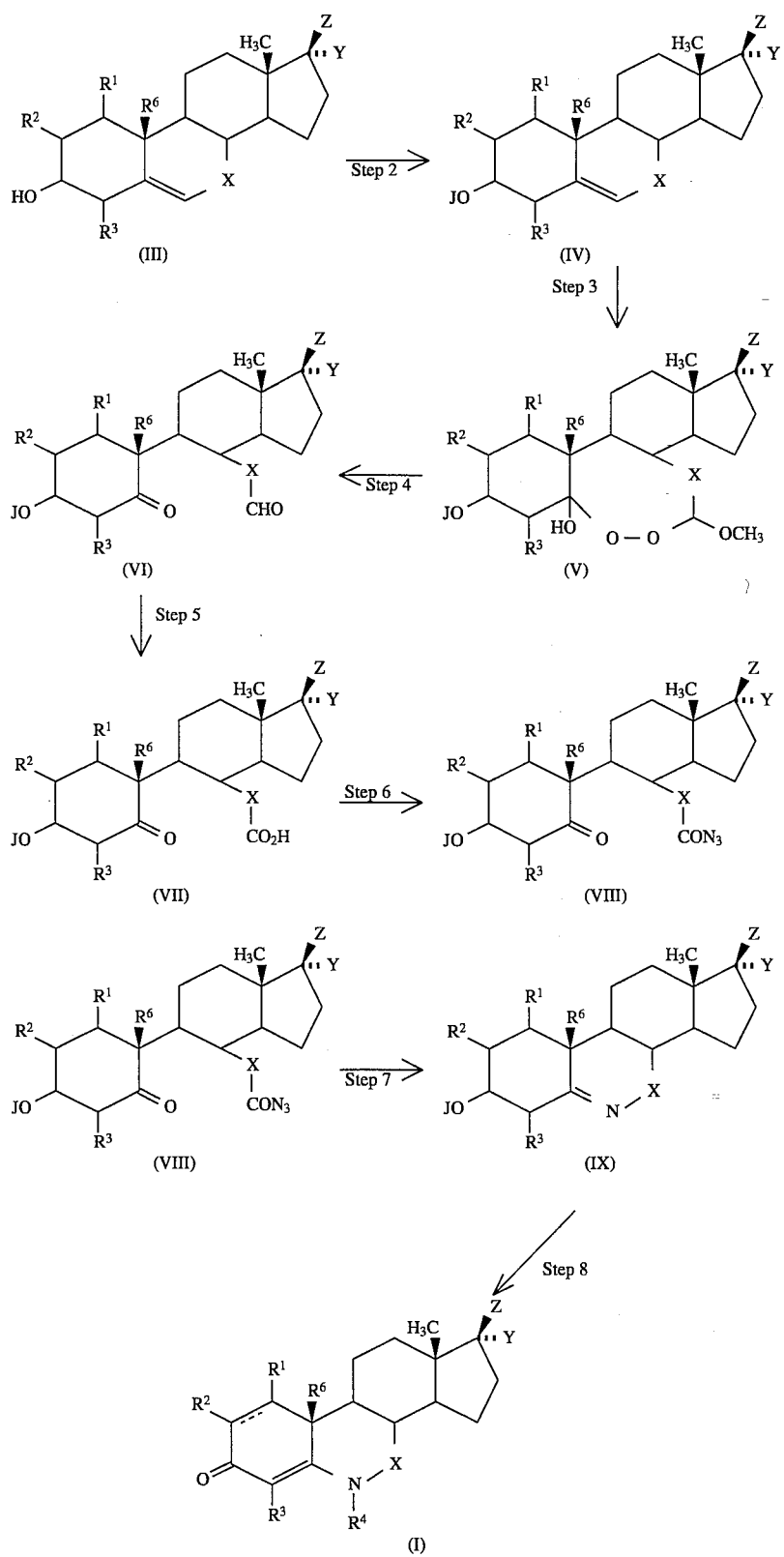
In Step 1 of Scheme I when Z is CO$_2$H, the acid group at the 17 position of a compound of formula (II) is converted to the corresponding ketone, ester or amide of compound (III) accompanied by deprotection of the hydroxy group at the 3 position. Alternatively a compound of formula (III) wherein Z is CO$_2$CH$_3$ and Y is H may be prepared from pregnenolone as described by Rasmusson, et al., *J. Med. Chem.*, 27, 1690 (1984).

This may be accomplished by activating the carboxylic acid group toward nucleophilic displacement by treatment with an activating agent such as N,N-bis[2-oxo-3-oxazolidinyl]phosphorinic chloride (BOP-Cl) or conversion to the corresponding acid halide group by treatment with a halogenating agent such as oxalyl chloride or thionyl chloride in an aprotic solvent such methylene chloride or toluene at $-5°$ to $10°$ C. The intermediate activated carboxylic acid, e.g., an acid chloride, may be reacted with $H-NR^{14}R^{15}$ or $HOR^5$ (wherein $R^5$, $R^{14}$ and $R^{15}$ are as defined for formula (I)) at room temperature in an aprotic solvent. When $R^5$ is alkyl, alkenyl, lower cycloalkyl, or adamantyl, the activated acid is treated with $R^5M$ (wherein M is a metal, such as magnesium or lithium) in a polar, aprotic solvent such as THF or diethyl ether containing catalytic CuI, at a temperature in the range of about $0°$ to about $-78°$ C.

In Step 2, a compound of formula (III) is treated with a suitable hydroxy protecting group such as for example a silicon derivative such as a trisubstituted silyl halide, a tetrahydropyran derivative or an aralkyl group such as a paramethoxybenzyl group. Typically the compound of formula (III) is treated with a trialkylsilyl halide, e.g., triisopropylsilyl chloride, at about $25°$ to $75°$ C. in an aprotic solvent such as dimethylformamide to protect the hydroxy group in the 3-position to yield the corresponding trisubstituted silylated compound of formula (IV).

In Step 3, a compound of formula (IV) is treated with ozone in methanol alone or as a mixture with one or more polar, protic or aprotic solvents, e.g., methylene chloride and methanol, at a temperature substantially below $0°$ C., e.g. from about $-50°$ to about $-80°$ C. to yield a corresponding compound of formula (V).

In Step 4, the compound of formula (V) in methanol alone or as a mixture with one or more polar, protic or aprotic solvents, e.g., methylene chloride and methanol, at about $-20°$ C. is treated with a reductant such as zinc and acetic acid then allowed to slowly warm to room temperature to yield the aldehyde of formula (VI). Alternatively the compound of formula (V) may be taken directly to step 5.

In Step 5, a compound of formula (V or VI) is reacted with an oxidant, such as Jones reagent (see Bowden, et al., *J. Chem. Soc.* 39, (1946)) at about $0°$ C., to yield the corresponding compound of formula (VII).

In Step 6, a compound of formula (VII) is converted to an activated carboxylate derivative such as an acid halide, e.g., chloride, by treatment with a halogenating agent, e.g. oxalyl chloride. The resulting acid halide is reacted with an alkali metal azide, e.g., sodium azide, at about $0°$ to $30°$ C. in an aqueous solvent mixture, such as water and acetone, to yield the corresponding acyl azide compound of formula (VIII).

Alternatively, the acid is treated with triphenyl phosphoryl azide in an aprotic solvent such as toluene to yield the acyl azide directly.

In Step 7, an acyl azide compound of formula (VIII) is rearranged with ring closure by warming to reflux in an aprotic solvent, such as toluene, to induce rearrangment to the corresponding isocyanate followed by stirring with a weak acid such as silica gel or by reaction with a strong, sterically hindered base, e.g., potassium t-butoxide, in a protic or aprotic solvent at a temperature in the range of about $90°$ to about $180°$ C. to generate the corresponding compound of formula (IX).

Finally, in Step 8, (general process A) a compound of formula (IX) is deprotected and oxidised. Thus, in general process (A1) compounds of general formula (I) wherein $R^4$ is hydrogen may be prepared by converting the protected hydroxy group of a compound of formula (IX) to the corresponding hydroxy group, i.e., the hydroxy group is deprotected in conventional manner. Thus, for example a trisubstituted silyl group may be removed by reaction of a compound of formula (IX) with aqueous hydrogen fluoride in a polar solvent such as acetonitrile at about $0°$ C. to room temperature. Next the hydroxy group is oxidized by reaction with a suitable oxidising agent, for example, with Jones reagent with migration of the double bond to the 4,5 position to generate the corresponding compound of formula (I) where $R^4$ is hydrogen.

Alternatively, in general process (A2) for the preparation of compounds of general formula (I) wherein $R^4$ is an acyl group the compound of formula (IX) is treated with an acylating agent such as di-t-butyldicarbonate to acylate the 6-nitrogen with migration of the double bond to the 4,5 position. The hydroxy protecting group is then removed in conventional manner, for example a trisubstituted silyl protecting group may be removed with a reagent such as tetrabutylammonium fluoride, and treated with an oxidant such as pyridinium dichromate to generate the corresponding compound of formula (I) where $R^4$ is t-butylcarboxy.

Alternatively, according to another general process (B) the compounds of formula (I) wherein X is

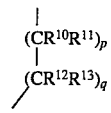

and both p and q are 1, and $R^{10}$, $R^{11}$, $R^{12}$ and $R^{13}$ are hydrogen, may be prepared by the procedure shown in Step 5 of Scheme II wherein $R^{1-6}$ are as defined for formula (I):

SCHEME II

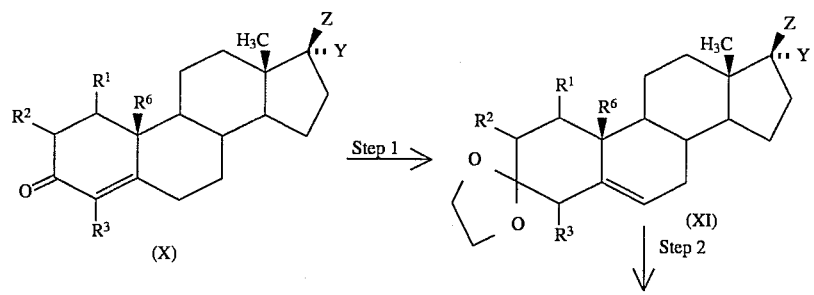

-continued
SCHEME II

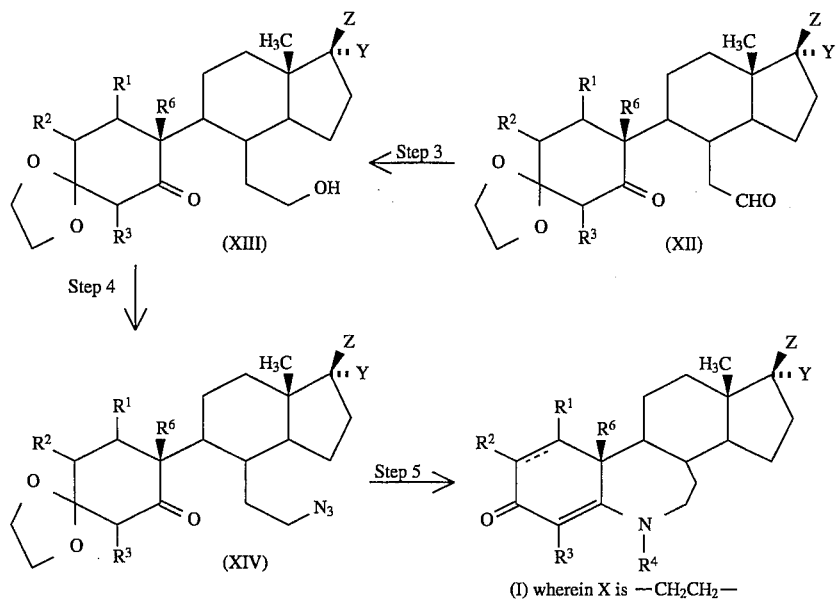

(I) wherein X is —CH$_2$CH$_2$—

In Step 1 of Scheme II, the enone function of compound (X) is protected as a ketal with concomitant migration of the double bond to the 5, 6 position by refluxing with ethylene glycol in the presence of an acid, such as p-toluenesulfonic acid, in a solvent such as toluene which allows azeotropic removal of water to yield the corresponding compound of formula (XI).

In Step 2, a compound of formula (XI) is treated with ozone in methanol alone or with one or more polar, protic or aprotic solvents mixtures, e.g., methylene chloride and methanol, at a temperature substantially below 0° C., e.g., from about −50° to about −80° C., followed by treatment at about −20° C. with a reductant, such as zinc and acetic acid, then allowed to slowly warm to room temperature to yield the aldehyde of formula (XII).

In Step 3, a compound of formula (XII) is reduced with a selective reducing agent, such as lithium tri-t-butoxyaluminumhydride in an aprotic solvent such as THF or diethyl ether to give the corresponding alcohol of formula (XIII).

In Step 4, the alcohol functionality of a compound of formula (XIII) is converted to a leaving group, such as the corresponding methanesulfonate by treatment with methanesulfonyl chloride in an aprotic solvent such as methylene chloride in the presense of a hindered tertiary amine base such as triethylamine. Once transformed to a leaving group, the alcohol is displaced by treatment with a source of azide, such as sodium azide, in a polar, aprotic solvent, such as DMF, to give the corresponding alkyl azide of formula (XIV).

In Step 5, a compound of formula (XIV) is treated with a reductant such as triphenylphosphine in THF at reflux followed by a strong protic acid such as 4M HCl to give the corresponding compound of formula (I) where X is —CH$_2$CH$_2$—.

Alternatively, according to another general process (C), a compound of formula (I) according to the invention may be converted into another compound of the invention using conventional procedures.

Thus, for example a double bond may be inserted between the carbon in the 1 position and the carbon in the 2 position by conventional means such as dehydrogenation with 2,3-dichloro-5,6-dicyano-1,4-benzoquinone by refluxing in an aprotic solvent such as dioxane to produce a compound of formula (I) which is unsaturated in the 1, 2 position. A compound of formula (I) with a double bond in the 1, 2 position may then be treated with the anion of trimethylsulfoxonium iodide, prepared by deprotonation with a base such as sodium hydride, in an aprotic, polar solvent such as DMSO to give a compound of formula (I) wherein R$^1$ and R$^2$ taken together form a cyclopropane ring.

Optionally a compound of formula (I) wherein R$^3$ is H and R$^4$ is acyl or acyloxy, such as t-butylcarboxy, may be treated with bromine at 0° C. in an aprotic solvent such as methylene chloride to give the corresponding compound of formula (I) wherein R$^3$ is Br, which may then be treated with an organotin species such as phenyltrimethyltin in the presence of a palladium catalyst such as PdCl$_2$(PPh$_3$)$_2$ and lithium chloride in a polar aprotic solvent such as dimethylformamide to give the corresponding compound of formula (I) wherein R$^3$ is methyl.

Additionally, a compound of formula (I) wherein R$^4$ is acyl or acyloxy, such as t-butylcarboxy, may be treated with a strong hindered base such as lithium diisoproylamide at −78° C. in an aprotic solvent such as THF followed by an electrophile, such as methyl iodide to give compounds of formula (I) wherein R$^2$ is methyl or lower alkyl.

Also, a compound of formula (I) wherein R$^3$ is H may be treated with cuprous cyanide or N,N-dimethylmethyleneammonium iodide in polar, aprotic solvents such as DMF or acetonitrile to give compounds of formula (I) wherein R$^3$ is —CN and —CH$_2$N(CH$_3$)$_2$ respectively.

Additionally a compound of formula (I) wherein R$^3$ is H may be treated with a halogenated succinimide such as N-iodosuccinimide in a solvent such as THF to give a compound of formula (I) wherein R$^3$ is I.

The compounds of formula (I) wherein R$^4$ is hydrogen may be reacted, via a nucleophilic reaction of the corresponding sodium or potassium salt, with L-lower alkyl, L-lower alkenyl, L-alkanoyl of 2 to 6 carbons, L-Alk$^1$, L-lower cycloalkyl, L-lower cycloalkyl-lower alkyl, cycloalkyl, L-(Alk$^1$)$_n$S(O)$_t$R$^7$, L-(Alk$^1$)$_n$-phthalimidyl, L-(Alk$^1$)-CO$_2$H, L-(Alk$^1$)$_n$-CO$_2$R$^7$, L-(Alk$^1$)$_n$-Ar$^1$, L-(Alk$^1$)$_n$-CONR$^8$R$^9$, L-(Alk$^1$)$_n$-NR$^8$R$^9$, L-(Alk$^1$)$_n$-OH or L-(Alk$^1$)$_n$-OR$^7$ at a temperature of about 5° to about 100° C. in a polar, aprotic solvent such as dimethylformamide, to yield the compounds of formula (I) wherein R$^4$ is other than hydrogen. The groups, R$^7$–R$^9$, Ar$^1$ and n, are as defined for formula (I) and L is a leaving group, such as defined in March, J., *Advanced Organic Chemistry*, 3d. Ed., 179, John Wiley & Sons. New York (1985) and in Hendrickson. J., et al., *Organic Chemistry*, 3d. Ed., 375–377, McGraw Hill, New York (1970), e.g. a halogen atom.

Additionally, a compound of formula (I) wherein Z is CO R$^7$, and in particular wherein R$^7$ is CH$_3$, may be treated with a strong base, such as lithium hydroxide in a solvent system such as THF or dioxane and water to give a compound of formula (I) where Z is CO$_2$H. An acid of this formula may then be treated as described in Step 1 to yield the corresponding compounds of formula (I) wherein Z is COR$^5$, CO$_2$R$^5$ or CONR$^{14}$R$^{15}$ Optionally, a compound of formula (I) wherein Z is CO$_2$R$^7$ and in particular wherein R$^7$ is CH$_3$, may be reduced with a reducing agent such as diisobutyl aluminum hydride and then reoxidized with Collins' reagent (CrO$_3$·2 pyridine) or another mild oxidant to produce a compound of formula (I) wherein Z is CHO, which may be treated with R$^{5'}$M (wherein M is a metal such as magnesium or lithium) and R$^{5'}$ is Alk$^1$-H, lower cycloalkyl or adamantyl to give, after oxidation with pyridinium dichromate, a compound of formula (I) wherein Z is COR$^5$.

Further, these compounds of formula (I), wherein Z is —CHO, may be treated with a Wittig reagent, such as Et$_2$OPOCH$_2$COR$^{5'}$, Et$_2$OPOCH$_2$CO$_2$R$^5$ or Et$_2$OPOCH$_2$CONR$^{14}$R$^{15}$ to give a compounds of formula (I) wherein Z is —CH=CH—COR$^{5'}$, CH=CH—CO$_2$R$^5$ or CH=CH—CONR$^{14}$R$^{15}$ respectively.

It will be appreciated by those skilled in this art that for certain substituents some Steps in the procedures shown in Scheme I and Scheme II are incompatible with survival of the functional groups of interest. In these cases, the substituents e.g. R$^3$ or Z is either introduced subsequent to the incompatible Step or is present in a protected form. An example of the former is the case where R$^3$ is halogen, in which case the halogen is introduced by reaction of a compound of formula (I) with a halogenated succinimide, such as N-bromosuccinimide. An example of the latter is the use of an ester or ether to protect a carboxylic acid or alcohol, respectively.

Thus, according to another general process (D), a compound of formula (I) according to the invention, or a salt thereof may be prepared by subjecting a protected derivative of formula (I) or a salt thereof to reaction to remove the protecting group or groups.

Thus, at an earlier stage in the preparation of a compound of formula (I) or a salt thereof it may have been necessary and/or desirable to protect one or more sensitive groups in the molecule to prevent undesirable side reactions.

The protecting groups used in the preparation of compounds of formula (I) may be used in conventional manner. See for example 'Protective Groups in Organic Chemistry' Ed. J. F. W. McOmie (Plenum Press 1973) or 'Protective Groups in Organic Synthesis' by Theedora W. Greene (John Wiley and Sons 1981).

Conventional amine protecting groups may include for example aralkyl groups, such as benzyl, diphenylmethyl or triphenylmethyl groups; and acyl groups such as N-benzyloxycarbonyl or t-butoxycarbonyl. Thus, compounds of general formula (I) wherein one or more of the groups R$^1$ and R$^2$ represent hydrogen may be prepared by deprotection of a corresponding protected compound.

Hydroxy groups may be protected, for example, by aralkyl groups, such as benzyl, diphenylmethyl or triphenylmethyl groups, acyl groups, such as acetyl, silicon protecting groups, such as trimethylsilyl or t-butyl dimethylsilyl groups, or as tetrahydropyran derivatives.

Removal of any protecting groups present may be achieved by conventional procedures. Thus an aralkyl group such as benzyl, may be cleaved by hydrogenolysis in the presence of a catalyst (e.g. palladium on charcoal); an acyl group such as N-benzyloxycarbonyl may be removed by hydrolysis with, for example, hydrogen bromide in acetic acid or by reduction, for example by catalytic hydrogenation; silicon protecting groups may be removed, for example by treatment with fluoride ion or by hydrolysis under acidic conditions; tetrahydropyran groups may be cleaved by hydrolysis under acidic conditions.

As will be appreciated, in any of the general processes (A) to (C) described above it may be necessary or desired to protect any sensitive groups in the molecule as just described. Thus, a reaction step involving deprotection of a protected derivative of general formula (I) or a salt thereof may be carried out subsequent to any of the above described processes (A) to (C).

Thus, according to a further aspect of the invention, the following reactions may, if necessary and/or desired by carried out in any appropriate sequence subsequent to any of the processes (A) to (C)

(i) removal of any protecting groups; and
(ii) conversion of a compound of formula (I) or a salt thereof into a pharmaceutically acceptable salt thereof.

Where it is desired to isolate a compound of the invention as a salt, for example as an acid addition salt, this may be achieved by treating the free base of general formula (I) with an appropriate acid, preferably with an equivalent amount, or with creatinine sulphate in a suitable solvent (e.g. aqueous ethanol).

As well as being employed as the last main step in the preparative sequence, the general methods indicated above for the preparation of the compounds of the invention may also be used for the introduction of the desired groups at an intermediate stage in the preparation of the required compound. It should therefore be appreciated that in such multi-stage processes, the sequence of reactions should be chosen in order that the reaction conditions do not affect groups present in the molecule which are desired in the final product.

The compound of formula (I) and the intermediate compounds, (II)–(XIV), shown in Schemes I and II may be purified by convenient methods of the art, e.g., chromatography or crystallization.

Steroid 5-α-Reductase in Vitro Assay

Enzyme activity may be determined using microsomes derived from prostate tissue of benign prostatic hypertrophy (BPH) patients or from rat prostate tissue. Prostatic microsomes were prepared by homogenization of the tissue, followed by differential centrifugation of the homogenate. Microsome extracts were incubated with 100 nM [1,2,6,7-$^3$H]-testosterone, 1 mM NADPH and varying amounts of the compounds of Formula (I), i.e., a test compound, for 60 minutes at 37° C. Corresponding incubations were carried out with no test compound as a control study. The percentage of conversion of testosterone to DHT in the presence of test compounds compared to the corresponding conversion in the control study was estimated using high pressure liquid chromatography (HPLC) with radiochemical detection. The results of this assay as IC$_{50}$ values for microsomes derived from human prostate and rat tissue are show in Table 1.

TABLE 1

5-α-REDUCTASE in vitro INHIBITORY ACTIVITY

| Compound/Example | IC$_{50}$ Human | ID$_{50}$ Rat |
|---|---|---|
| 1 | +++ | ++ |
| 2 | +++ | ++ |
| 3 | +++ | ++ |
| 4 | +++ | + |
| 5 | +++ | ++ |
| 6 | ++ | + |
| 7 | +++ | nt |
| 8 | +++ | ++ |
| 9 | +++ | + |
| 10 | ++ | + |
| 11 | ++ | + |
| 12 | + | nt |
| 13 | + | nt |
| 14 | + | nt |
| 15 | + | nt |
| 16 | +++ | ++ |
| 17 | +++ | + |
| 18 | +++ | ++ |
| 19 | +++ | +++ |
| 20 | +++ | +++ |
| 21 | +++ | + |
| 22 | + | nt |
| 23 | ++ | + |
| 24 | ++ | + |
| 25 | + | nt |
| 26 | +++ | ++ |
| 27 | ++ | + |
| 28 | ++ | + |
| 29 | ++ | + |
| 30 | +++ | ++ |
| 31 | +++ | ++ |
| 32 | ++ | + |
| 33 | ++ | + |
| 34 | ++ | nt |
| 35 | +++ | + |
| 36 | +++ | + |
| 37 | + | nt |
| 38 | + | nt |
| 39 | +++ | nt |
| 40 | + | nt |
| 41 | + | nt |
| 42 | + | nt |
| 43 | + | nt |
| 44 | + | nt |
| 45 | + | nt |
| 46 | + | nt |
| 47 | + | nt |
| 48 | + | nt |
| 49 | + | nt |
| 50 | + | nt |
| 51 | + | nt |
| 52 | + | nt |
| 53 | + | nt |
| 54 | + | nt |
| 55 | +++ | +++ |
| 56 | ++ | +++ |
| 57 | ++ | +++ |
| 58 | +++ | ++ |
| 59 | +++ | + |
| 60 | ++ | +++ |
| 61 | ++ | ++ |
| 62 | ++ | ++ |
| 63 | +++ | ++ |
| 64 | +++ | ++ |
| 65 | +++ | ++ |
| 66 | +++ | ++ |
| 67 | +++ | +++ |
| 68 | ++ | + |
| 69 | ++ | + |
| 70 | ++ | nt |
| 71 | +++ | nt |
| 72 | +++ | nt |
| 73 | +++ | +++ |
| 74 | +++ | ++ |
| 75 | ++ | + |
| 76 | ++ | ++ |
| 77 | ++ | + |

+++ = <10 nM
++ = 10–100 nM
+ = 100–1000 nM
nt = not tested

In Vivo Evaluation of Steroid 5-α-Reductase Inhibitors

The in vivo activity of steroid 5α-reductase inhibitors may be determined in both acute and chronic rat models. The acute model utilizes castrated male rats that receive testosterone (1 mg) subcutaneously and test compound (10 mg/kg) p.o., at 0.5 hr. and 4.5 hr. prior to sacrifice, respectively. Levels of DHT in the serum and prostate indicate the ability of the test compound to inhibit-steroid 5α-reductase in an acute rat model. Known steroid 5α-reductase inhibitors were tested in parallel to ensure consistency of the assay method.

The chronic model also utilizes castrated male rats that are dosed daily with testosterone (20 μg/rat) subcutaneously and with test compound (0.01–10 mg/kg) p.o. for 7 days. The animals are then sacrificed and their prostates weighed. Reduction in the size of testosterone-stimulated prostate weight demonstrated activity of the test compound. Known steroid 5α-reductase inhibitors were tested in parallel to ensure consistency of the assay method.

In view of the reported species' differences between human and rat steroid 5α-reductase in vivo, results were tempered by comparison of the in vitro activity against rat and human enzymes. These procedures were supported by pharmacokinetic studies for compounds with predictable reduced efficacy in the rat model.

Utility

The steroid 5α-reductase inhibitors of the present invention are useful in the treatment of androgen responsive diseases, e.g., benign and malignant diseases of the prostate, especially benign prostatic hypertrophy. For correlation of in vitro, rat in vivo and human clinical data relating to an inhibitor of 5α-reductase, see Stoner, J. *Steroid Biochem. Molec. Biol.*, 37, 375 (1990); Brooks, et al., *Steroids*, 47, 1 (1986) and Rasmusson, *J. Med. Chem.*, 29, 2298 (1986)). They are also useful in the treatment of prostatitis, prostate cancer, androgen mediated diseases of the skin, such as acne, hirsutism and male pattern baldness. Other hormone related diseases, e.g., polycystic ovary disease, would be expected to respond to treatment with these inhibitors.

The amount of compound of formula (I) required to be effective as an 5α-reductase inhibitor will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, and the particular compound to be administered. However, a suitable effective 5α-reductase inhibitory dose is in the range of about 0.1 to about 50 mg/kg body weight per day, preferably in the range of about 0.5 to about 20 mg/kg per day. The total daily dose may be given as a single dose, multiple doses, e.g., two to six times per day, or by intravenous infusion for a selected duration. Dosages above or below the range cited above are within the scope of the present invention and may be administered to the individual patient if desired and necessary.

For example, for a 75 kg mammal, a dose range would be about 50 to about 1500 mg per day, and a typical dose would be about 200 mg per day. If discrete multiple doses are indicated, treatment might typically be 50 mg of a compound of formula (I) given 4 times per day.

Formulations

Formulations of the present invention for medical use comprise an active compound, i.e., a compound of formula (I), together with an acceptable carrier thereof and optionally other therapeutically active ingredients. The carrier must be pharmaceutically acceptable in the sense of being compatible with the other ingredients of the formulation and not deleterious to the recipient thereof.

The present invention, therefore, further provides a pharmaceutical formulation comprising a compound of formula (I) together with a pharmaceutically acceptable carrier thereof.

The formulations include those suitable for oral, rectal or parenteral (including subcutaneous, intramuscular and intravenous) administration. Preferred are those suitable for oral or parenteral administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier and then, if necessary, shaping the product into desired unit dosage form.

Formulations of the present invention suitable for oral administration may be presented as discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredient(s) may include flavoring, an agent to retard crystallization of the sugar or an agent to increase the solubility of any other ingredient, e.g. as a polyhydric alcohol, for example, glycerol or sorbitol.

Formulations for rectal administration may be presented as a suppository with a conventional carrier, e.g., cocoa butter or Witepsol S55 (trademark of Dynamite Nobel Chemical, Germany), for a suppository base.

For transdermal administration the compounds according to the invention may be formulated as creams, gels, ointments or lotions or as a transdermal patch. Such compositions may for example be formulated with an aqueous or oily base with the addition of suitable thickening, gelling, emulsifying, stabilising, dispersing, suspending, and/or colouring agents.

Formulations suitable for parenteral administration conveniently comprise a sterile aqueous preparation of the active compound which is preferably isotonic with the blood of the recipient. Such formulations suitably comprise a solution or suspension of a pharmaceutically and pharmacologically acceptable acid addition salt of a compound of the formula (I) that is isotonic with the blood of the recipient. Thus, such formulations may conveniently contain distilled water, 5% dextrose in distilled water or saline and a pharmaceutically and pharmacologically acceptable acid addition salt of a compound of the formula (I) that has an appropriate solubility in these solvents, for example the hydrochloride, isothionate and methanesulfonate salts, preferably the latter. Useful formulations also comprise concentrated solutions or solids containing the compound of formula (I) which upon dilution with an appropriate solvent give a solution suitable for parental administration above.

In addition to the aforementioned ingredients, the formulations of this invention may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

EXAMPLES

The following examples illustrate aspects of this invention but should not be construed as limitations. The symbols and conventions used in these examples are consistent with those used in the contemporary chemical literature, for example, the *Journal of the American Chemical Society*.

Example 1

17β-N,N-Diethylcarbamoyl-6-azaandrost-4-en-3-one (Compound 1)

A. 3β-Acetoxyetionic acid diethylamide

To a solution of 3β-acetoxyetionic acid (*Org. Syn.* 5, 8) (21.46 g, 60 mmol) in methylene chloride (150 mL) under nitrogen is added triethylamine (16.6 mL, 120 mmol), the reaction mixture is stirred for 10 minutes and then cooled to 0° C. Next N,N-bis[2-oxo-3-oxazolidinyl]phosphorinic chloride (BOP-Cl, 15.3 g, 60 mmol) and diethylamine (6.8 mL, 66 mmol) are added and the reaction allowed to warm to room temperature overnight. An aqueous solution of 1N HCl (100 mL) and isopropanol (50 mL) is then added, the mixture stirred 10 min, chloroform is added (500 mL) and the organic layers washed sequentially with 1N HCl, water and saturated aqueous NaCl. The solution is then dried over MgSO$_4$, concentrated to a yellow solid which is dissolved in ethyl acetate (150 mL), boiled with activated charcoal, filtered through silica gel and concentrated to give 3β-acetoxyetienic acid diethylamide as an off-white solid; yield: 16.6 g (67%) of sufficient purity to carry on to the following steps.

B. 3β-Hydroxyetionic acid diethylamide

A solution of 3β-acetoxyetionic acid diethylamide (10.03 g, 24 mmol) in anhydrous methanol (250 mL) is treated with anhydrous potassium carbonate (5.0 g) and heated to reflux under nitrogen for 1 hour. The methanol is removed by rotary evaporation, the solid dissolved in ethyl acetate (300 mL), washed sequentially with water and saturated aqueous NaCl then dried over MgSO$_4$, concentrated and flash chromatographed on silica gel (0 to 20% ethyl acetate to give 3β-hydroxyetionic acid diethylamide as a white solid; yield: 8.95 g (100%)

C. 3β-Triisopropylsilyloxyetionic acid diethyl amide

To a solution of 3β-hydroxyetionic acid diethyl amide (8.95 g, 24 mmol) in dimethylformamide (DMF, 25 mL) is added imidazole (4.10 g, 60 mmol) and triisopropylsilyl chloride (10.3 mL, 48 mmol) and the reaction heated to 60° C. for about 5 hr. The DMF is then removed by rotary evaporation, diethyl ether added (100 mL), and the solution washed with 1N HCl, saturated aqueous NaCl, dried over $MgSO_4$ and concentrated by rotary evaporation. The resulting concentrate is flash chromatographed on silica gel (0 to 20% ethyl acetate/hexanes) to give 3β-triisopropylsilyloxyetionic acid diethyl amide as a white foam; yield: 10.28 g (80%).

D. A solution of 3β-triisopropylsilyloxyetionic acid diethyl amide (10.28 g, 19 mmol), from part C, in methylene chloride (400 mL) and methanol (300 mL) is cooled to −78° C. and treated with ozone until a deep blue color persists. The reaction is then warmed to room temperature, concentrated and flash chromatographed on silica gel (15 to 25% ethyl acetate/hexanes) to give the peroxy compound of formula (V) [wherein $R^1$, $R^2$, $R^3$ and Y are hydrogen, and Z is $CONEt_2$] as a white foam; yield: 8.70 g (74%); FAB mass spec. $MH^+$ 610.

E. The compound prepared in part D, above, (8.70 g, 14 mmol) is dissolved in acetone and treated with Jones reagent (12 mL, 3.22M, 39 mmol) at 0° C. for 15 min. Next, isopropanol (25 mL) is added, the acetone removed by rotary evaporation, ethyl acetate added (100 mL) and the solution washed with $H_2O$ and saturated aqueous NaCl. The solution is then dried over $MgSO_4$, concentrated and the residue flash chromatographed on silica gel (15 to 50% ethyl acetate/hexanes) to give the corresponding keto-acid compound of formula (VII) as a white solid; yield 4.09 g (50%); FAB mass spec. $MH^+$ 578.

F. A solution of the keto-acid compound of formula (VII) prepared in part E, above, (3.58 g, 6.2 mmol) in methylene chloride (50 mL) at 0° C. is treated with anhydrous pyridine (1.5 mL) and oxalyl chloride (1.62 mL, 18.6 mmol). After 30 min the reaction is concentrated, eventually at high vacuum, dissolved in acetone (100 mL) and treated with sodium azide (2.0 g, 31 mmol) in $H_2O$ (7 mL). After 30 min the reaction is concentrated, the residue dissolved in ethyl acetate, washed with $H_2O$, saturated aqueous NaCl, dried over $MgSO_4$ and concentrated to give corresponding acyl azido compound of formula (VIII) as a white foam; yield: 3.45 g (92%).

G. 17β-N,N-Diethylcarbamoyl-3β-triisopropylsilyloxy-6-azaandrost-5-ene

The acyl azido compound of formula (VIII) prepared in part F, above, (3.45 g, 5.7 mmol) is dissolved in toluene (40 mL), heated at reflux for 30 min, concentrated, dissolved in t-butanol (100 mL) containing catalytic potassium t-butoxide and heated at reflux for 20 min. After cooling to room temperature, diethyl ether (200 mL) is added, the organics washed with $H_2O$ and saturated aqueous NaCl, the solution dried over $MgSO_4$, concentrated and flash chromatographed on silica gel (50 to 100% ethyl acetate/hexanes) to give 17β-N,N-diethylcarbamoyl- 3β-triisopropylsilyloxy-6-azaandrost-5-ene (a compound of formula (IX) as a light yellow solid; yield: 2.66 g (81%); FAB mass spec. $MH^+$ 531.

H. 17β-N,N-Diethylcarbamoyl-6-azaandrost-4-en-3-one

A solution of 17β-N,N-diethylcarbamoyl-3β-triisopropylsilyloxy-6-azaandrost-5-ene (1.51 g, 2.8 mmol) in acetonitrile (100 mL) at 0° C. is treated with 48% aqueous HF (20 mL), the reaction allowed to warm to room temperature and stirred for 2 hours. The solution is then diluted with methylene chloride (200 mL), washed with $H_2O$ and saturated aqueous bicarbonate, dried over $MgSO_4$ and concentrated to an off-white solid; yield 1.02 g crude (96%). A solution of this solid (0.48 g, 1.3 mmol) in acetone (100 mmol) is treated with Jones reagent (1 mL, 3.22M, 3.2 mmol) and warmed to room temperature. Next, isopropanol is added (10 mL), the reaction concentrated, the residue dissolved in ethyl acetate (75 mL), washed with saturated aqueous bicarbonate, dried over $MgSO_4$ and concentrated to give 17β-N, N-diethylcarbamoyl-6-azaandrost-4-en-3-one as an off-white solid; yield: 0.22 g (46%). This material is then triturated with ether to give 172 mg pure white solid; m.p. 253°–256° C. (dec.). Anal. Calcd. for $C_{23}H_{36}N_2O_2$; C, 74.15; H, 9.74; N, 7.52. Found: C, 73.88; H, 9.77; N, 7.44.

Example 2

17β-N,N-Diethylcarbamoyl-6-methyl-6-azaandrost-4-en-3-one (Compound 2)

To a solution of 17β-N,N-diethylcarbamoyl-6-azaandrost-4-en-3-one (24 mg, 0.065 mmol) in DMF (2 mL) at room temperature is added NaH (16 mg, 80% oil dispersion, 0.5 mmol) and, after 30 min, methyl iodide (50 μL, excess). After stirring for 30 min ethyl acetate (30 mL) is added, the solution washed with $H_2O$ and saturated aqueous NACl, dried over $MgSO_4$, concentrated and flash chromatographed on silica gel (100% ethyl acetate to 5% methanol/chloroform) to give 17β-N,N-diethylcarbamoyl-6-methyl-6-azaandrost-4-en-3-one as a white solid; yield 19 mg (76%). This material is then recrystallized from hexanes/methylene chloride to give 14 mg pure white solid; m.p. 158°–159° C. Anal. Calcd. for $C_{24}H_{38}N_2O_2$; C, 74.57; H, 9.91; N, 7.25. Found: C, 74.38; H, 9.84; N, 7.18.

Example 3

17β-N-t-Butylcarbamoyl-6-azaandrost-4-en-3-one (Compound 3)

A. 3β-triisopropylsilyloxyetionic acid methyl ester

A suspension of 3β-hydroxyetionic acid methyl ester, (J. Med. Chem., 27, 1690 (1984)), (516 g, 1.55 mol) in DMF (800 mL) is heated to 55° C., imidazole (264 g, 3.88 mol) added with vigorous mechanical stirring, followed by dropwise addition of triisopropylsilyl chloride (360 g, 1.87 mol). The reaction becomes homogeneous after about half of the triisopropylsilyl chloride is added and the reaction temperature increases to ca. 70° C. The reaction is complete by TLC (35% ethyl acetate/hexanes) after 1.5 hrs and a thick slurry forms. The reaction is then worked up as in Example 1, part C and crystallized from hexanes/methanol to give 3β-triisopropylsilyloxyetionic acid methyl ester as a white crystalline solid; yield: 667 g (88%); m.p. 124°–125° C. Anal. Calcd. for $C_{30}H_{52}O_3Si$; C, 73.71; H, 10.72. Found: C, 73.79; H, 10.74.

B. A solution of 3β-triisopropylsilyloxyetionic acid methyl ester (166 g, 0.34 mol), from part A, in methylene chloride (2 L) and methanol (800 mL) is cooled to −78° C. and treated with ozone until a blue color persists. The peroxy compound of formula (V) may be isolated as in Example 1, part D and recrystallized from hexanes to give an analytical sample; m.p. 119°–121° C. Anal. Calcd. for $C_{31}H_{56}O_7Si$; C, 65.45; H, 9.92. Found: C, 65.37; H, 9.86. However, more conveniently, the reaction is allowed to warm to −50° C. under a stream of nitrogen, and zinc dust added (89 g, 1.36 mol), followed by glacial acetic acid (150 mL). The reaction is then allowed to warm to room temperature with stirring, filtered to remove zinc, the solution washed with water, saturated aqueous NaCl, saturated aqueous bicarbonate, dried over MgSO$_4$ and concentrated by rotary evaporation to give crude keto-aldehyde of formula (VI) as a white foam; yield: 176 g (99%).

C. The compound prepared in part B above (176 g, 0.34 mol) is oxidized with Jones reagent as in Example 1, part E to give the corresponding keto-acid of formula (VII) as an off-white solid; yield: 163 g (89%). Recrystallization from ethyl acetate/hexanes gives a white crystalline solid; m.p. 143°–145° C. Anal. Calcd. for C$_{30}$H$_{52}$O$_6$Si; C, 67.12; H, 9.76. Found: C, 67.21; H, 9.80.

D. 17β-Carbomethoxy-3β-triisopropylsilyloxy-6-azaandrost-5-ene

A portion of the keto-acid of formula (VII) prepared above (77 g, 0.14 mol) is converted to the acyl-azide as in Example 1, part F, and is then dissolved in toluene (500 mL), heated to reflux for 5 minutes, cooled to 50° C. and treated with silica gel (150 g). The reaction is allowed to stir overnight, the silica gel removed by filtration and washed with 4:1 ethyl acetate/methanol (500 mL) to give 17β-carbomethoxy- 3β-triisopropylsilyloxy-6-azaandrost-5-ene (a compound of formula ((IX)) as a white foam; yield: 66 g (94%). Flash chromatography on silica gel (30% ethyl acetate/hexanes) gives an analytical sample as a white foam. Anal. Calcd. for C$_{29}$H$_{51}$NO$_3$Si; C, 71.11; H, 10.49; N, 2.86: Found: C, 71.04; H, 10.51; N, 2.80.

E. 17β-Carbomethoxy-6-t-butylcarboxy-6-azaandrost-4-en-3-one

Crude 17β-carbomethoxy-3β-triisopropylsilyloxy-6-azaandrost-5-ene (66 g, 0.135 mol) is dissolved in pyridine (500 mL), treated with di-t-butyldicarbonate (150 g, 0.69 mol) and allowed to stir overnight. The pyridine is removed by rotary evaporation and tetrabutylammonium fluoride (500 mL, 1M, 0.5 mol) in tetrahydrofuran (THF) added carefully and the reaction heated to reflux for 5 min. The THF is removed by rotary evaporation, the residue dissolved in ethyl acetate (500 mL), washed cautiously with water, saturated aqueous NaCl, dried with MgSO$_4$ and concentrated. This material is dissolved in DMF (500 mL), is treated with pyridinium dichromate (153 g, 0.41 mol) and allowed to stir overnight. The reaction is poured into water (700 mL) and extracted with ethyl acetate (2×500 mL). The combined extracts are washed with water, 5% aqueous CuSO$_4$, saturated aqueous NaCl, dried over MgSO$_4$, concentrated and flash chromatographed (0–60%, diethyl ether/ hexanes) to give 17β-carbomethoxy-6-t-butylcarboxy-6-azaandrost-4-en-3-one as an off-white foam; yield: 37.5 g (64%); FAB mass spec. MH$^+$ 432.

F. 17β-Carboxy-6-t-butylcarboxy-6-azaandrost-4-en-3-one

A solution of 17β-carbomethoxy-6-t-butylcarboxy-6-azaandrost-4-en-3-one (15.4 g, 36 mmol), from part E, in dioxane (150 mL) and water (100 mL) is treated with LiOH•H$_2$O (3.31 g, 79 mmol) and stirred overnight on a water bath. The reaction is poured into saturated aqueous NaHSO$_4$ (150 mL), extracted with methylene chloride (3×100 mL), extracts washed with saturated aqueous NaCl, dried over MgSO$_4$ and concentrated to a volume of 100 mL. At this point crystals begin to form and 2:1 hexanes/ethyl acetate (50 mL) is added, the mixture triturated, cooled to room temperature and 17β-carboxy-6-t-butylcarboxy-6-azaandrost-4-en-3-one collected as a fluffy white powder; yield: 9.44 g (63%); m.p. 215°–216° C. Anal. Calcd. for C$_{24}$H$_{35}$NO$_5$•1/4H$_2$O; C, 68.30; H, 8.48; N, 3.32. Found: C, 68.45; H, 8.41; N, 3.28.

The mother liquor is diluted with methylene chloride (100 mL), filtered through silica gel, the silica gel washed with 1:1 diethyl ether/hexanes and the eluant. concentrated to give recovered 17β-carbomethoxy-6-t-butylcarboxy-6-azaandrost-4-en-3-one; yield: 2.63 g (17%). The silica pad is then washed with 1:9 methanol/methylene chloride (250 mL), the eluant concentrated, the resulting solid triturated with 2:1 hexanes/ethyl acetate (50 mL), cooled to 0° C. and 17β-carboxy- 6-t-butylcarboxy-6-azaandrost-4-en-3-one collected as a white powder; yield: 2.25 g (15%). The combined yield based on recovered starting material is 94%.

G. 17β-N-t-Butylcarbamoyl-6-azaandrost-4-en-3-one

A sample of 17β-carboxy-6-t-butylcarboxy-6-azaandrost-4-en-3-one (2.03 g, 4.86 mmol), from part F, is coupled with t-butyl amine as described in Example 1, part A, to give crude 17β-N-t-butylcarbamoyl-6-t-butylcarboxy-6-azaandrost-4-en-3-one which is dissolved in methylene chloride (30 mL) and treated with trifluoroacetic acid (4 mL) at room temperature. After 3 hrs the reaction is concentrated, methylene chloride (50 mL) and saturated aqueous bicarbonate (50 mL) added, the layers separated, methylene chloride washed with saturated aqueous NaCl, dried over MgSO$_4$, concentrated and chromatographed on silica gel (0–10% methanol/methylene chloride) to give 17β-N-t-butylcarbamoyl-6-azaandrost-4-en-3-one as a white solid; yield: 1.04 g (57%). Recrystallization from methylene chloride/hexanes gives an analytical sample as a white crystalline solid; m.p. 186°–189° C. Anal. Calcd. for C$_{23}$H$_{36}$N$_2$O$_2$•3/8H$_2$O; C, 72.83; H, 9.77; N, 7.38. Found C, 72.95; H, 9.85; N, 7.22.

Example 4

17β-(2-Pyridinylthiocarbonyl)-6-azaandrost-4-en-3-one (Compound 4)

A solution of 17β-carboxy-t-butylcarboxy-6-azaandrost-4-en-3-one (486 mg. 1.16 mmol), Example 3, part F, is dissolved in toluene (10 mL) and treated with triphenylphosphine (458 mg, 1.75 mmol) and dipyridinyl disulfide (385 mg, 1.75 mmol) at room temperature. After stirring overnight the reaction is poured into ethyl acetate (100 mL), washed with saturated aqueous NaHSO$_4$, 2N NaOH and water, dried over MgSO$_4$, concentrated and chromatographed on silica gel (60% ethyl acetate/hexanes) to give crude 17β-(2-pyridinylthiocarbonyl)-6-t-butylcarboxy-6-azaandrost-4-en- 3-one. This material is dissoved in methylene chloride (15 mL) and treated with trifluoroacetic acid (5 mL) and after 2 hrs is worked up as in Example 3, part G and triturated with diethyl ether to give 17β-(2-pyridinylthiocarbonyl)- 6-azaandrost-4-en-3-one as a light yellow solid; yield: 181 mg (41%); m.p. 190°–202° C. Anal. Calcd. for C$_{24}$H$_{30}$N$_2$O$_2$S•1/4H$_2$O; C, 69.45; H, 7.41; N, 6.75; S, 7.72. Found: C, 69.55; H, 7.31; N, 6.76; S, 7.72.

Example 5

17β-(1-Oxo-3-methylbutyl)6-azaandrost-4-en-3-one (Compound 5)

A. 17β-Hydroxymethyl-3β-hydroxy-6-t-butylcarboxy-6-azaandrost-4-ene

A solution of 17β-carbomethoxy-6-t-butylcarboxy-6-azaandrost-4-en-3-one (2.30 g, 5.33 mmol), Example 3, part E, in methylene chloride (70 mL) at −78° C. is treated with diisobutylaluminum hydride (1.5M in toluene, 15 mL, 22.5 mmol). After 20 minutes the reaction is quenched with methanol (4 mL), methylene chloride added (150 mL), washed with 2N NaOH and water, dried over MgSO$_4$ and concentrated to give crude 17β-hydroxymethyl-3β-hydroxy-6-t-butylcarboxy-6-azaandrost-4-ene of sufficient purity to carry on to the following steps; yield: 2.16 g (99%).

B. 17β-Formyl-6-t-butylcarboxy-6-azaandrost-4-en-3-one

A solution of 17β-hydroxymethyl-3β-hydroxy-6-t-butylcarboxy-6-azaandrost-4-ene (182 mg, 0.448 mmol), prepared in part A above, in methylene chloride (7 mL) is added to freshly prepared Collins' reagent. ($CrO_3$•2 pyridine) in methylene chloride (12 mL) at 0° C. After 15 minutes the solvent is decanted from the tar, the tar is triturated with methylene chloride (2×30 mL), the combined methylene chloride washed with 2N NaOH, saturated aqueous $NaHSO_4$, saturated aqueous NaCl, dried over $MgSO_4$, concentrated and chromatographed on silica gel (50% ehtyl acetate/hexanes) to give crude 17β-formyl-6-t-butylcarboxy-6-azaandrost-4-en-3-one of sufficient purity to carry on to the following steps; yield: 125 mg (69%).

C. 17β-(1-Hydroxy-3-methylbutyl)-6-t-butylcarboxy-6-azaandrost-4-en-3-one

A solution of 17β-formyl-6-t-butylcarboxy-6-azaandrost-4-en-3-one (550 mg, 1.37 mmol), prepared in part B above, in THF (10 mL) is treated with isobutylmagnesium bromide (2.0M in diethyl ether, 2.0 mL, 4.0 mmol) at 0° C. After 20 minutes the reaction is quenched with saturated aqueous $NaHSO_4$, extracted with ethyl acetate (2×40 mL), dried over $MgSO_4$, concentrated and chromatographed on silica gel (50% ethyl acetate/hexanes) to give crude 17β-(1-hydroxy-3-methylbutyl)-6-t-butylcarboxy-6-azaandrost-4-en-3-one of sufficient purity to carry on to the following steps; yield: 168 mg (26%); FAB mass spec. $MH^+$ 460.

D. 17β-(-1-Oxo-3-methylbutyl)-6-azaandrost-4-en-3-one

A solution of 17β-(1-hydroxy-3-methylbutyl)-6-t-butylcarboxy-6-azaandrost-4-en-3-one (160 mg, 0.349 mmol) prepared in part C above, in DMF (10 mL) is treated with pyridinium dichromate (656 mg, 1.74 mmol) at room temperature. After 10 hrs the reaction is poured into water, extracted with ethyl acetate (2×50 mL), the extracts are dried over $MgSO_4$, concentrated and chromatographed on silica gel (40% ethyl acetate/hexanes) to give crude 17β-(1 -oxo-3-methylbutyl)-6-t-butylcarboxy- 6-azaandrost-4-en-3-one; yield: 135 mg (85%). A portion of this material (81 mg, 0.18 mmol) is treated with trifluoroacetic acid as described in Example 4 above to give, after recrystallization from diethyl ether/hexanes 17β-(1-oxo- 3-methylbutyl)-6-azaandrost-4-en-3-one as a white crystalline solid; yield: 58 mg (92%); m.p. 169°–171° C. Anal. Calcd. for $C_{23}H_{35}NO_2$•1/4$H_2O$; C, 76.30; H, 9.88; N, 3.87. Found: C, 76.48; h, 9.93; N, 3.89.

Alternatively, a solution of 17β-carboxy-6-t-butylcarboxy-6-azaandrost-4-en-3-one (260 mg, 0.62 mmol), example 3, Part F, is dissolved in toluene (10 mL) and treated with pyridine (3 eq) and catalytic dimethylformamide, cooled to 0° C., and thionyl chloride added (80 µL, 1.10 mmol). The reaction is then allowed to warm to room temperature and is stirred for 1 hr. The solids are then removed by filtration, the solution concentrated, the resulting crude acid chloride dissolved in THF (6 mL), CuL added (120 mg, 0.62 mmol), cooled to –78° C. and treated with isobutylmagnesium bromide (2.0M in diethyl ether, 0.5 mL, 1 mmol). The reaction is allowed to warm to room temperature, stirred for 30 min and is worked up as in Part C above to give 17β-(1-oxo-3-methylbutyl)-6-azaandrost-4-en-3-one.

Example 6

17β-N,N-Diethylcarbamoyl-6-azaandrost-1,4-dien-3-one (Compound 6)

A. 17β-Carbomethoxy-6-t-butylcarboxy-6-azaandrost-1,4-dien-3-one

A solution of 17β-carbomethoxy-6-t-butylcarboxy-6-azaandrost-4-en-3-one (2.00 g, 4.63 mmol), prepared in Example 3, part E, in dioxane (50 mL) is treated with 2,3-dichloro-5,6-dicyano-1,4-benzoquinone (DDQ, 1.37 g, 6.02 mmol) and p-nitrophenol (10 mg). The reaction is heated to reflux for 2 hrs, poured into ice water (150 mL), extracted with ethyl acetate (3×100 mL), extracts washed with saturated aqueous $NaHSO_3$, 2N NaOH, saturated aqueous NaCl, dried over $MgSO_4$, concentrated and chromatographed on silica gel (40% ethyl acetate/hexanes) to give crude 17β-carbomethoxy-6-t-butylcarboxy-6-azaandrost-1,4-dien-3-one as a tan solid of sufficient purity to carry on to the following steps; yield: 1.53 g (76%).

B. 17β-N,N-Diethylcarbamoyl-6-t-butylcarboxy-6-azaandrost-1,4-dien-3-one

The crude 17β-carbomethoxy-6-t-butylcarboxy-6-azaandrost-1,4-dien-3-one (1.50 g, 3.50 mmol), prepared in part A, is hydrolyzed as in Example 3, part F and then coupled with diethylamine as described in Example 1, part A to give after chromatography (50% ethyl acetate/hexanes) 17β-N,N-diethylcarbamoyl-6-t-butylcarboxy- 6-azaandrost-1,4-dien-3-one as a white foam; yield: 1.07 g (65%). Anal. Calcd. for $C_{28}H_{42}N_2O_4$; C, 71.45; H, 9.00; N, 5.95. Found C, 71.38; H, 9.07; N, 5.90.

C. 17β-N,N-Diethylcarbamoyl-6-azaandrost-1,4-dien-3-one

A sample of 17β-N,N-diethylcarbamoyl-6-t-butylcarboxy-6-azaandrost-1,4-dien-3-one (188 mg, 0.400 mmol), prepared in part B above, is treated with trifluoroacetic acid as described in Example 4 above to give, after trituration with diethyl ether/hexanes 17β-N,N-diethylcarbamoyl-6-azaandrost-1,4-dien-3-one as a pale yellow solid; yield: 98 mg (66%); m.p.>250° C. Anal. Calcd. for $C_{23}H_{34}N_2O_2$•1/2$H_2O$; C, 72.78; H, 9.29; N, 7.38. Found: C, 72.89; H, 9.20; N, 7.43.

Example 7

17β-N,N-Diethylcarbamoyl-6-azaandrost-1α,2α-cyclopropyl-4-en-3-one (Compound 7)

A solution of 17β-N,N-diethylcarbamoyl-6-t-butylcarboxy-6-azaandrost-1,4-dien-3-one (500 mg, 1.06 mmol) prepared as described in Example 6, part B, in dimethylsufoxide (DMSO, 4 mL) is added to a solution of trimethylsulfoxonium iodide (1.31 g, 5.93 mmol) which has stirred with sodium hydride (60% dispersion in oil; 237 mg, 5.93 mmol) in DMSO (4 mL) for one hour. After stirring overnight at room temperature the reaction is poured into ice water, extracted with diethyl ether (2×50 mL), extracts washed with saturated aqueous NaCl, dried over $MgSO_4$ and concentrated to a white foam; yield: 411 mg (80%). This material is treated with trifluoroacetic acid as described in Example 4 above to give, after crystallization from diethyl ether/hexanes 17β-N,N-diethylcarbamoyl-6-azaandrost-1α,2α-cyclopropyl-4-en-3-one as a pale yellow solid; yield: 186 mg (57%); m.p.>250° C. Anal. Calcd. for $C_{24}H_{36}N_2O_2$•1/4$H_2O$; C, 74.08; H, 9.45; N, 7.20. Found: C, 74.01; H, 9.40; N, 7.11.

Example 8

17β-N,N-Diethylcarbamoyl-6-azaandrost-4-chloro-4-en-3-one (Compound 8)

A solution of 17β-N,N-diethylcarbamoyl-6-azaandrost-4-en-3-one (compound 1) (152 mg, 0.408 mmol) in THF (3 mL) is treated with N-chlorosuccinimide (110 mg, 0.82 mmol). After 4 hrs at room temperature the reaction is quenched with saturated aqueous Na$_2$SO$_3$, diluted with water, extracted with methylene chloride (2×30 mL), dried over MgSO$_4$, concentrated and chromatographed (0–30% i-propanol in 70% ethyl acetate/hexanes) to give 17β-N,N-diethylcarbamoyl-6-azaandrost- 4-chloro-4-en-3-one as a yellow solid; yield: 81 mg (49%); m.p. 134°–136° C. Anal. Calcd. for C$_{23}$H$_{35}$N$_2$O$_2$Cl•3/4H$_2$O; C, 65.70; H, 8.75; N, 6.66. Found: C, 65.91; H, 8.96; N, 6.14.

Example 9

17β-N,N-Diethylcarbamoyl-6-azaandrost-4-bromo-4-en-3-one (Compound 9)

This compound is prepared from 17β-N,N-diethylcarbamoyl-6-azaandrost-4-en-3-one (compound 1) by treatment with N-bromosuccinimide as described in Example 8 to give 17β-N,N-diethylcarbamoyl-6-azaandrost-4-bromo-4-en-3-one as a white powder; m.p. 205°–207° C. Anal. Calcd. for C$_{23}$H$_{35}$N$_2$O$_2$Br; C, 61.19; H, 7.81; N, 6.21. Found:C, 61.19; H, 8.15; N, 5.96.

Example 10

7β-N,N-Diethylcarbamoyl-6-azaandrost-4-iodo-4-en-3-one (Compound 10)

This compound is prepared from 17β-N,N-diethylcarbamoyl-6-azaandrost-4-en-3-one (compound 1) by treatment with N-iodosuccinimide as described in Example 8 to give 17β-N,N-diethylcarbamoyl-6-azaandrost-4-iodo-4-en-3-one as pale yellow crystals; m.p. 195°–197° C. Anal. Calcd. for C$_{23}$H$_{35}$N$_2$O$_2$I; C, 55.42; H, 7.08; N, 5.62. Found: C, 55.42; H, 7.13: N, 5.54.

Example 11

17β-N,N-Diethylcarbamoyl-6-azaandrost-4-methyl-4-en-3-one (Compound 11)

A. 17β-N,N-Diethylcarbamoyl-6-t-butylcarboxy-6-azaandrost-4-bromo-4-en-3-one

A solution of 17β-N,N-diethylcarbamoyl-6-t-butylcarboxy-6-azaandrost-4-en-3-one (5.20 g, 11.0 mmol), [prepared from coupling 17β-carboxylic acid-6-butylcarboxy-6-azaandrost-4-en-3-one (Example 3, part F) and diethylamine as described in Example 1, part A], in methylene chloride (100 mL) containing anhydrous K$_2$CO$_3$ (10 g, 74 mmol) at 0° C. is treated with bromine (1.7 mL, 33 mmol) dissolved in methylene chloride (10 mL). After 2 hrs the mixture is diluted with water extracted with methylene chloride (3×50 mL), extracts washed with saturated aqueous Na$_2$SO$_3$, dried over MgSO$_4$, concentrated and chromatographed (50–70% ethyl acetate/hexanes) to give 17β-N,N-diethylcarbamoyl- 6-t-butylcarboxy-6-azaandrost-4-bromo-4-en-3-one as a white solid; yield: 5.18 g (85%). Recrystallization from ethyl acetate gives an analytical sample; m.p. 215°–216° C. (decomp.) Anal. Calcd. for C$_{28}$H$_{43}$N$_2$O$_4$Br; C, 60.97; H, 7.86; N, 5.08. Found.: C, 60.98; H; 7.92; N, 5.01.

B. 17β-N,N-Diethylcarbamoyl-6-azaandrost-4-methyl-4-en-3-one

A mixture of 17β-N,N-diethylcarbamoyl-6-t-butylcarboxy-6-azaandrost-4-bromo-4-en-3-one (250 mg, 0.453 mmol), prepared in part A, phenyltrimethyltin (320 mg, 1.33 mmol), PdCl$_2$(PPh$_3$)$_2$(45 mg) and lithium chloride (20 mg) in DMF (1.5 mL) is heated at 140° C. for 8 hrs. The reaction is allowed to cool to room temperature, quenched with 5M aqueous potassium fluoride (5 mL), extracted with ethyl acetate (3×30 mL), extracts washed with 5M aqueous potassium flouride, dried over MgSO$_4$, concentrated and chromatographed (20–70% ethyl acetate/hexanes) to give 17β-N,N-diethylcarbamoyl-6-t-butylcarboxy-6-azaandrost-4-methyl-4-en-3-one as a clear oil; yield: 204 mg (93%). A portion of this material (181 mg, 0.372 mmol)is treated with trifluoroacetic acid as described in Example 4 above to give, after chromatography (0–30% i-propanol in 70% ethyl acetate/hexanes), 17β-N,N-diethylcarbamoyl-6-azaandrost-4-methyl-4-en-3-one as a white powder; yield: 75 mg (52%); m.p. 115°–118° C. Anal. Calcd. for C$_{24}$H$_{38}$N$_2$O$_2$•1/2i-propanol; C, 73.51; H, 10.16; N, 6.72. Found: C, 73.79; H, 10.21; N, 6.79.

Example 12

17β-N,N-Diethylcarbamoyl-6-azaandrost-4-ethyl-4-en-3-one (Compound 12)

A mixture of 17β-N,N-diethylcarbamoyl-6-t-butylcarboxy-6-azaandrost-4-bromo- 4-en-3-one (510 mg, 0.925 mmol), prepared in Example 11, part A, vinyltributyltin (800 mg, 2.52 mmol), PdCl$_2$(PPh$_3$)$_2$ (70 mg) and lithium chloride (50 mg)in DMF (1.5 mL)is heated at 140° C. for 4 hrs. The reaction is allowed to cool to room temperature, quenched with 5M aqueous potassium flouride (3 mL), extracted with ethyl acetate (2×30 mL), extracts washed with 5M aqueous potassium fluoride, dried over MgSO$_4$, concentrated and chromatographed (20–70% ethyl acetate/hexanes) to give 17β-N,N-diethylcarbamoyl-6-t-butylcarboxy-6-azaandrost-4-vinyl-4-en-3-one as a white foam; yield 395 mg (84%). A portion of this material (180 mg, 0.353 mmol) is dissolved in i-propanol and treated with 20% palladium hydroxide on carbon (100 mg) and cyclohexene (2 mL) at reflux for 8 hrs. The reaction is then filtered, concentrated and chromatographed (50% ethyl acetate/hexanes) to give 17β-N,N-diethylcarbamoyl-6-t-butylcarboxy-6-azaandrost- 4-ethyl-4-en-3-one as an amorphous solid; yield: 173 mg (96%); m.p. 163°–165° C. A portion of this material (157 mg, 0.306 mmol) is treated with trifluoroacetic acid as described in Example 4 above to give, after chromatography (0–50% i-propanol in 70% ethyl acetate/hexanes), 17β-N,N-diethylcarbamoyl-6-azaandrost- 4-ethyl-4-en-3-one as a white powder; yield: 85 mg (67%); m.p. 112°–116° C. Anal. Calcd. for C$_{25}$H$_{40}$N$_2$O$_2$•3/8i-propanol; C, 74.16; H, 10.24; N, 6.62. Found: C, 74.16; H, 10.28; N, 67.30.

Example 13

17β-N,N-Diethylcarbamoyl-6-azaandrost-4-cyano-4-en-3-one (Compound 13)

A solution of 17β-N,N-diethylcarbamoyl-6-t-butylcarboxy-6-azaandrost-4-bromo- 4-en-3-one (300 mg, 0.544 mmol), prepared in Example 11, part A, in DMF (2 mL) is treated with cuprous cyanide (292 mg, 3.25 mmol) at 140° C. for 4 hrs. The reaction is allowed to cool to room temperature, diluted with aqueous 5% sodium cyanide, extracted with ethyl acetate (3×20 mL), the extracts washed with saturated aqueous NaCl, dried over MgSO$_4$, concentrated and chromatographed (0–30% i-propanol in 70% ethyl acetate/hexanes) and recrystallized from ethyl acetate to give 17β-N,N-diethylcarbamoyl-6-azaandrost-4-cyano-4-en-3-one as a tan solid; yield: 94 mg (43%); m.p.<240° C. Anal. Calcd. for C$_{24}$H$_{35}$N$_3$O$_2$Br; C, 72.51; H, 8.87; N, 10.57. Found: C, 72.27; H, 8.91; N, 10.52.

Example 14

17β-N,N-Diethylcarbamoyl-6-azaandrost-4-dimethylaminomethylene-4-en-3-one (Compound 14)

A solution of 17β-N,N-diethylcarbamoyl-6-azaandrost-4-en-3-one (compound 1) (160 mg, 0.430 mmol) in acetonitrile (2 mL) is treated with N,N-dimethylmethyleneammonium iodide (Eschenmoser's salt, 160 mg, 0.865 mmol) at room temperature for 4 hrs. The reaction is diluted with saturated aqueous sodium bicarbonate, extracted with ethyl acetate (2×30 mL), the extracts washed with saturated aqueous NaCl, dried over MgSO$_4$, concentrated and chromatographed (30% i-propanol in 70% ethyl acetate/hexanes followed by 10% ammonium hydroxide in 20% acetonitrile/chloroform) to give 17β-N,N-diethylcarbamoyl- 6-azaandrost-4-dimethylaminomethylene-4-en-3-one as a white solid; yield 110 mg (60%); m.p. 84°–88° C. Anal. Calcd. for C$_{26}$H$_{43}$N$_3$O$_2$·1/4H$_2$O; C, 71.93; H, 10.10; N, 9.68. Found: C, 72.18; H, 10.05; N, 9.67.

Examples 15–78

Following the procedures of Example 1, part A or Example 3, part G for preparation of amides as the Z substituent in compounds of formula (I); the procedure of Example 2 for introduction of R$^4$ substituents in compounds of formula (I); the procedure of Example 5 for preparation of ketones as the Z substituent i compounds of formula (I); the procedure of Example 8 and 11 for introduction of R$^3$ substituents in compounds of formula (I); and the procedures of Example 6, part A or Example 7 for introduction of unsaturation or cyclopropyl substitution in the 1,2-position of compounds of formula (I) the following compounds are prepared: (in some cases a simple deprotection step is necessary to reveal the functionality incorporated in the R$^4$ substituent and methods widely known in the art are utilized (cf. Green, "Protective Groups in Organic Synthesis" *Wiley-Interscience*, 1981.)

Example 15

17β-N,N-Diethylcarbamoyl-6-(3-hydroxypropyl)-6-azaandrost-4-en-3-one (Compound 15)

Melting Point: 223°–225° C. Anal. Calcd. for C$_{26}$H$_{42}$N$_2$O$_3$; C, 72.51; H, 9.83; N, 6.51. Found: C, 72.60; H, 9.81; N, 6.43.

Example 16

17β-N,t-Butylcarbamoyl-6-methyl-6-azaandrost-4-en-3-one (Compound 16)

Melting Point: 254°–256° C. Anal. Calcd. for C$_{24}$H$_{38}$N$_2$O$_2$; C, 74.57; H, 9.91; N, 7.25. Found: C, 74.33; H, 9.92; N, 7.17.

Example 17

17β-N,N-Diisopropylcarbamoyl-6-azaandrost-4-en-3-one (Compound 17)

Melting Point: 140°–150° C. Anal. Calcd. for C$_{25}$H$_{40}$N$_2$O$_2$·H$_2$O; C, 71.96; H, 9.66; N, 5.60 Found: C, 72.13; H, 9.81; N, 5.57

Example 18

17β-N,N-Diisopropylcarbamoyl-6-methyl-6-azaandrost-4-en-3-one (Compound 18)

FAB mass spec. for C$_{26}$H$_{42}$N$_2$O$_2$; 414.64 Found: 415 MH$^+$

Example 19

17β-N-1-Adamantylcarbamoyl-6-azaandrost-4-en-3-one (Compound 19)

Melting Point: 197°–199° C. Anal. Calcd. for C$_{29}$H$_{42}$N$_2$O$_2$·1/2H$_2$O; C, 75.76; H, 9.43; N, 6.10. Found: C, 75.79; H, 9.43; N, 6.09.

Example 20

17β-N-1-Adamantylcarbamoyl-6-methyl-6-azaandrost-4-en-3-one (Compound 20)

Melting Point: 262°–264° C. Anal. Calcd. for C$_{30}$H$_{44}$N$_2$O$_2$; C, 77.54; H, 9.54; N, 6.03. Found: C, 77.48; H, 9.70; N, 5.96.

Example 21

17β-N-Methoxy-N-methylcarbamoyl-6-azaandrost-4-en-3-one (Compound 21)

Melting Point: 230° C. (decomp) Anal. Calcd. for C$_{21}$H$_{32}$N$_2$O$_3$; C, 69.97; H, 8.95; N, 7.77. Found: C, 69.89; H, 9.00; N, 7.80.

Example 22

17β-N-Piperizinocarbamoyl-6-azaandrost-4-en-3-one (Compound 22)

Melting Point: <280° C. Anal. Calcd. for C$_{23}$H$_{35}$N$_3$O$_2$·1/2H$_2$O; C, 70.02; H, 9.20; N, 10.65. Found: C, 70.25; H, 9.26; N, 10.38.

Example 23

17β-N-Morpholinocarbamoyl-6-azaandrost-4-en-3-one (Compound 23)

Melting Point: 274° C. (decomp). Anal. Calcd. for C$_{23}$H$_{34}$N$_2$O$_3$·H$_2$O; C, 68.28; H, 8.97; N, 6.92. Found: C, 68.03; H, 8.97; N, 6.70.

Example 24

17β-Carbomethoxy-6-azaandrost-4-en-3-one (Compound 24)

Melting Point: 254°–257° C. (decomp).

Example 25

17β-Carboxy-6-methyl-6-azaandrost-4-en-3-one (Compound 25)

Melting Point: 238° C. (decomp). Anal. Calcd. for C$_{20}$H$_{29}$NO$_3$·CF$_3$CO$_2$H; C, 59.32; H, 6.79; N, 3.14. Found: C, 59.29; H, 7.13; N, 3.46.

Example 26

17β-(1-Oxo-3-methylbutyl)-6-methyl-6-azaandrost-4-en-3-one (Compound 26)

Melting Point: 40°–46° C. ESI mass spec. for $C_{24}H_{37}NO_2$; 372.2903 MH$^+$ Found: 372.2890 MH$^+$

Example 27

17β-N,N-Diethylcarbamoyl-6-methyl-6-azaandrost-1,4-dien-3-one (Compound 27)

Melting Point: 151°–152° C. Anal. Calcd. for $C_{24}H_{36}N_2O_2$; C, 74.96; H, 9.44; N, 7.29. Found: C, 74.86; H, 9.49; N, 7.28.

Example 28

17β-N-t-Butylcarbamoyl-6-azaandrost-1,4-dien-3-one (Compound 28)

Melting Point: 196°–198° C. Anal. Calcd. for $C_{23}H_{34}N_2O_2 \cdot 1/4H_2O$; C, 72.78; H, 9.29; N, 7.38. Found: C, 72.85; H, 9.24; N, 7.55.

Example 29

17β-N-t-Butylcarbamoyl-6-methyl-6-azaandrost-1,4-dien-3-one (Compound 29)

Melting Point: 174°–175° C. Anal. Calcd. for $C_{24}H_{36}N_2O_2 \cdot 1/2H_2O$; C, 74.09; H, 9.46; N, 7.20. Found: C, 73.72; H, 9.66; N, 6.87.

Example 30

17β-N-1-Adamantylcarbamoyl-6-azaandrost-1,4-dien-3-one (Compound 30)

Melting Point: 188° C. (decomp). Anal. Calcd. for $C_{30}H_{40}N_2O_2 \cdot 1/2H_2O$; C, 76.11; H, 8.81; N, 6.12. Found: C, 76.03; H, 9.01; N, 6.09.

Example 31

17β-N-1-Adamantylcarbamoyl-6-methyl-6-azaandrost-1,4-dien-3-one (Compound 31)

Melting Point: 242°–243° C. Anal. Calcd. for $C_{30}H_{42}N_2O_2$; C, 77.88; H, 9.15; N, 6.06. Found: C, 77.33; H, 9.12; N, 5.91.

Example 32

17β-N,N-Diethylcarbamoyl-6-methyl-6-azaandrost-1α,2α-cyclopropyl-4-en-3-one (Compound 32)

Melting Point: 213°–215° C. Anal. Calcd. for $C_{25}H_{38}N_2O_2 \cdot 1/4H_2O$; C, 74.49; H, 9.63; N, 6.95. Found: C, 74.44; H, 9.62; N, 6.89.

Example 33

17β-N-t-Butylcarbamoyl-6-azaandrost-1α,2α-cyclopropyl-4-en-3-one (Compound 33)

Melting Point: foams below 100° C. Anal. Calcd. for $C_{24}H_{36}N_2O_2 \cdot 1/2H_2O$; C, 73.24; H, 9.48; N, 7.12. Found: C, 73.47; H, 9.63; N, 7.13.

Example 34

17β-N-t-Butylcarbamoyl-6-methyl-6-azaandrost-1α,2α-cyclopropyl-4-en-3-one (Compound 34).

Melting Point: 228°–231° C. Anal. Calcd. for $C_{25}H_{38}N_2O_2$; C, 75.33; H, 9.61; N, 7.03. Found: C, 75.10; H, 9.65; N, 6.93.

Example 35

17β-N,N-Diethylcarbamoyl-6-ethyl-6-azaandrost-4-en-3-one (Compound 35)

Melting Point: 174°–176° C. Anal. Calcd. for $C_{25}H_{40}N_2O_2$; C, 74.95; H, 10.07; N, 6.99. Found: C, 74.69; H, 10.12; N, 6.93.

Example 36

17β-N,N-Diethylcarbamoyl-6-propyl-6-azaandrost-4-en-3-one (Compound 36)

Melting Point: 158°–160° C. Anal. Calcd. for $C_{26}H_{42}N_2O_2$; C, 75.31; H, 10.21; N, 6.76. Found: C, 75.19; H, 10.23; N, 6.72.

Example 37

17β-N,N-Diethylcarbamoyl-6-butyl-6-azaandrost-4-en-3-one (Compound 37)

Melting Point: 170°–172° C. Anal. Calcd. for $C_{27}H_{44}N_2O_2$; C, 75.65; H, 10.35; N, 6.54. Found: C, 75.47; H, 10.27; N, 6.54.

Example 38

17β-N,N-Diethylcarbamoyl-6-hexyl-6-azaandrost-4-en-3-one (Compound 38)

Melting Point: 94°–97° C. Anal. Calcd. for $C_{29}H_{48}N_2O_2$; C, 76.26; H, 10.59; N, 6.14. Found: C, 76.34 H, 10.56; N, 6.14.

Example 39

17β-N,N-Diethylcarbamoyl-6-isopropyl-6-azaandrost-4-en-3-one (Compound 39)

Melting Point: 165°–168° C. Anal. Calcd. for $C_{26}H_{42}N_2O_2 \cdot 1/2H_2O$; C, 73.71; H, 9.99; N, 6.61. Found: C, 73.96; H, 10.00; N, 6.69.

Example 40

17β-N,N-Diethylcarbamoyl-6-isobutyl-6-azaandrost-4-en-3-one (Compound 40)

Melting Point: 198°–201° C. Anal. Calcd. for $C_{27}H_{44}N_2O_2 \cdot 1/4H_2O$; C, 74.86; H, 10.35; N, 6.47. Found: C, 74.81; H, 10.22; N, 6.47.

Example 41

17β-N,N-Diethylcarbamoyl-6-methylenecyclopropyl-6-azaandrost-4-en-3-one (Compound 41)

Melting Point: 180°–182° C. Anal. Calcd. for $C_{27}H_{42}N_2O_2$; C, 74.43; H, 9.95; N, 6.43. Found: C, 74.65; H, 9.89; N, 6.48.

Example 42

17β-N,N-Diethylcarbamoyl-6-allyl-6-azaandrost-4-en-3-one (Compound 42)

Melting Point: 145°–146° C. Anal. Calcd. for $C_{25}H_{40}N_2O_2$; C, 75.68; H, 9.77; N, 6.79. Found: C, 75.81; H, 9.87; N, 6.63.

Example 43

17β-N,N-Diethylcarbamoyl-6-benzyl-6-azaandrost-4-en-3-one (Compound 43)

Melting Point: 193°–194° C. Anal. Calcd. for $C_{30}H_{42}N_2O_2$; C, 77.88; H, 9.15; N, 6.05. Found: C, 77.72; H, 9.15; N, 5.98.

Example 44

17β-N,N-Diethylcarbamoyl-6-(2-acetic acid)-6-azaandrost-4-en-3-one (Compound 44)

Melting Point: 237°–238° C. (decomp.) Anal. Calcd. for $C_{25}H_{38}N_2O_2$; C, 69.74; H, 8.90; N, 6.51. Found: C, 69.53; H, 8.95; N, 6.55.

Example 45

17β-N,N-Diethylcarbamoyl-6-(3-propanoic acid)-6-azaandrost-4-en-3-one (Compound 45)

Anal. Calcd. for $C_{26}H_{39}N_2O_4 \cdot 7/2H_2O$; C, 60.80; H, 9.03; N, 5.45. Found: C, 61.20; H, 8.05; N, 5.10.

Example 46

17β-N,N-Diethylcarbamoyl-6-(methyl-3-propanoate)-6-azaandrost-4-en-3-one (Compound 46)

FAB mass spec for $C_{27}H_{42}N_2O_2$; 458.33. Found: 459 $MH^+$

Example 47

17β-N,N-Diethylcarbamoyl-6-(4-butanoic acid)-6-azaandrost-4-en-3-one (Compound 47)

Anal. Calcd. for $C_{27}H_{41}N_2O_4 \cdot Li \cdot 3H_2O$; C, 62.53; H, 9.13; N, 5.40. Found: C, 62.42; H, 8.28; N, 5.33.

Example 48

17β-N,N-Diethylcarbamoyl-6-(5-pentanoic acid)-6-azaandrost-4-en-3-one (Compound 48)

Melting Point: 187° C. (decomp.) Anal. Calcd. for $C_{28}H_{43}N_2O_4 \cdot Li \cdot 2H_2O$; C, 65.35; H, 9.21; N, 5.44. Found: C, 64.83; H, 8.83; N, 5.53.

Example 49

17β-N,N-Diethylcarbamoyl-6-(methyl-5-pentanoate)-6-azaandrost-4-en-3-one (Compound 49)

FAB Mass spec for $C_{29}H_{46}N_2O_4$; 486.36. Found: 487 $MH^+$.

Example 50

17β-N,N-Diethylcarbamoyl-6-(6-hexanoic acid)-6-azaandrost-4-en-3-one (Compound 50)

Melting Point: 163° C. (decomp.) Anal. Calcd. for $C_{29}H_{45}N_2O_4 \cdot Li \cdot 7/2H_2O$; C, 62.45; H, 8.43; N, 5.08. Found: C, 62.68; H, 9.43; N, 5.04.

Example 51

17β-N,N-Diethylcarbamoyl-6-(ethyl-6-hexanoate)-6-azaandrost-4-en-3-one (Compound 51)

FAB mass spec for $C_{31}H_{50}N_2O_4$; 514.39. Found: 515 $MH^+$.

Example 52

17β-N,N-Diethylcarbamoyl-6-(3-phthalimidylpropyl)-6-azaandrost-4-en-3-one (Compound 52)

Melting Point: 108°–110° C. Anal. Calcd. for $C_{34}H_{45}N_3O_4 \cdot 1/2H_2O$; C, 71.80; H, 8.15; N, 7.39. Found: C, 71.96; H, 8.05; N, 7.43.

Example 53

17β-N,N-Diethylcarbamoyl-6-(4-phthalimidylbutyl)-6-azaandrost-4-en-3-one (Compound 53)

Melting Point: 105°–107° C. Anal. Calcd. for $C_{35}H_{47}N_3O_4$; C, 73.27; H, 8.26; N, 7.32. Found: C, 73.07; H, 8.24; N, 7.33.

Example 54

17β-N,N-Diethylcarbamoyl-6-(2-methoxyethyl)-6-azaandrost-4-en-3-one (Compound 54)

Melting Point: 108°–110° C. Anal. Calcd. for $C_{26}H_{42}N_2O_3$; C, 72.51; H, 9.83; N, 6.51. Found: C, 72.58; H, 9.88; N, 6.49.

Example 55

17β-N-1-Adamantylcarbamoyl-6-azaandrost-4-bromo-4-en-3-one (Compound 55)

Melting Point: 181°–187° C. (decomp.) Anal. Calcd. for $C_{29}H_{41}N_2O_2Br$; C, 65.76; H, 7.81; Br, 15.10; N, 5.29 Found: C, 65.59; H, 7.82; Br, 15.00; N, 5.23

Example 56

17β-N-1-Adamantylcarbamoyl-6-azaandrost-4-methyl-4-en-3-one (Compound 56)

Melting Point: 169°–175° C. (decomp.) Anal. Calcd. for $C_{30}H_{44}N_2O_2$; C, 77.53; H, 9.55; N, 6.03. Found: C, 77:42, H, 9.62; N, 5.96.

Example 57

17β-N-1-Adamantylcarbamoyl-6-methyl-6-azaandrost-4-methyl-4-en-3-one (Compound 57)

Melting Point: 150°–155° C. Anal. Calcd. for $C_{31}H_{46}N_2O_2 \cdot 1/4H_2O$; C, 75.63; H, 9.73; N, 5.69. Found: C, 75.36, H, 9.39; N, 5.71.

Example 58

17β-N-Diphenylmethylcarbamoyl-6-azaandrost-4-en-3-one (Compound 58)

Melting Point: 192°–194° C. Anal. Calcd. for $C_{32}H_{38}N_2O_2$; C, 79.63; H, 7.94; N, 5.80. Found: C, 79.38, H, 7.99; N, 5.72.

Example 59

17β-N-Diphenylcarbamoyl-6-azaandrost-4-en-3-one (Compound 59)

Melting Point: 154° C. Anal. Calcd. for $C_{31}H_{36}N_2O_2 \cdot 3/2H_2O$; C, 75.11; H, 7.93; N, 5.65. Found: C, 75.02, H, 7.79; N, 5.58.

Example 60

17β-N-exo-2-Norbornylmethylcarbamoyl-6-azaandrost-4-en-3-one (Compound 60)

Melting Point: 179° C. (decomp.) Anal. Calcd. for $C_{27}H_{40}N_2O_2 \cdot 6/5H_2O$; C, 72.67; H, 9.58; N, 6.28. Found: C, 72.56, H, 9.68; N, 6.41.

Example 61

17β-N-endo-2-Norbornylcarbamoyl-6-azaandrost-4-en-3-one (Compound 61)

Melting Point: 188° C. (decomp.) Anal. Calcd. for $C_{26}H_{38}N_2O_2 \cdot 3/2H_2O$; C, 71.36; H, 9.44; N, 6.40. Found: C, 71.50, H, 9.19; N. 6.42.

Example 62

17β-N-t-Butylcarbamoyl-6-azaandrost-4-methyl-4-en-3-one (Compound 62)

Melting Point: 168°–169° C. Anal. Calcd. for $C_{24}H_{38}N_2O_2$; C, 74.57; H, 9.91; N, 7.25. Found: C, 74.48, H, 9.93; N, 7.21.

Example 63

17β-N-Thiomorpholinocarbamoyl-6-azaandrost-4-en-3-one (Compound 63)

Melting Point: 276°–277° C. Anal. Calcd. for $C_{23}H_{34}N_2O_2S$; C, 68.62; H, 8.51; N, 6.96. Found: C, 68.46, H, 8.53; N, 6.95.

Example 64

17β-(1-Oxo-3-methylbutyl)-6-azaandrost-4-methyl-4-en-3-one (Compound 64)

Melting Point: 187°–189° C. Anal. Calcd. for $C_{24}H_{37}N_2O_2$; C, 77.58; H, 10.03; N, 3.76. Found: C, 77.27, H, 9.96; N, 3.83.

Example 65

17β-N-Benzylcarbamoyl-6-azaandrost-4-en-3-one (Compound 65)

Melting Point: 149°–150° C. Anal. Calcd. for $C_{32}H_{36}N_2O_2 \cdot H_2O$; C, 73.55; H, 8.55; N, 6.60. Found: C, 73.01, H, 8.50; N, 6.47.

Example 66

17β-(1-Oxo-3-methylbutyl-6-azaandrost-4-bromo-4-en-3-one (Compound 66)

Melting Point: 197°–200° C. Anal. Calcd. for $C_{23}H_{34}N_2O_2Br \cdot 1/2H_2O$; C, 62.02; H, 7.92; N, 3.14. Found: C, 61.92, H, 7.64; N, 3.12.

Example 67

17β-N-1-Anthracylcarbamoyl-6-azaandrost-4-en-3-one (Compound 67)

Melting Point: 210°–213° C. Anal. Calcd. for $C_{33}H_{36}N_2O_2 \cdot 1/2H_2O$; C, 79.01; H, 7.43; N, 5.58. Found: C, 79.01, H, 7.49; N, 5.62.

Example 68

17β-N,N-Diethylcarbamoyl-6-methyl-6-azaandrost-4-methyl-4-en-3-one (Compound 68)

Melting Point: 180°–182° C. Anal. Calcd. for $C_{25}H_{40}N_2O_2 \cdot 1/4H_2O$; C, 74.12; H, 9.95; N, 6.92. Found: C, 74.30, H,10.13; N, 6.87.

Example 69

17β-N-t-Butylcarbamoyl-6-methyl-6-azaandrost-4-methyl-4-en-3-one (Compound 69)

Melting Point: 122°–124° C. Anal. Calcd. for $C_{25}H_{40}N_2O_2$; 400.61. Found: 401 MH⁺.

Example 70

17β-N,N-Diethylcarbamoyl-6-azaandrost-4-fluoro-4-en-3-one (Compound 70)

FAB mass spec. for Point: $C_{23}H_{35}N_2O_2F$; 390. Found: 391 MH⁺.

Example 71

17β-N-Triphenylmethylcarbamoyl-6-azaandrost-4-en-3-one (Compound 71)

Melting Point: 186°–194° C. Anal. Calcd. for $C_{38}H_{42}N_2O_2 \cdot H_2O$; C, 79.13; H, 7.69; N, 4.86. Found: C, 79.18, H, 7.69; N, 4.86.

Example 72

17β-N-1-Napthylcarbamoyl-6-azaandrost-4-en-3-one (Compound 72)

Melting Point: 198°–204° C. Anal. Calcd. for $C_{29}H_{34}N_2O_2 \cdot 1/2H_2O$; C, 74.17; H, 7.94; N, 5.96. Found: C, 74.30, H, 7.71; N, 5.96.

Example 73

17β-Carbo-(2-adamantyl)-oxy-6-azaandrost-4-en-3-one (Compound 73)

A suspension of 17β-carboxy-6-t-butylcarboxy-6-azaandrost-4-en-3-one (760 mg, 1.82 mmol) in toluene (20 mL) is cooled to 0° C. and treated with pyridine (225 mL, 2.78 mmol) and thionyl chloride (200 mL, 2.74 mmol). After stirring 1 hr at 0° C., the suspension is concentrated to a tan solid and the solid is dissolved in dichloromethane (20 mL). The resulting tan solution is treated with 2-adamantanol (301 mg, 1.98 mmol). After stirring overnight, the reaction is diluted with dichloromethane, washed with saturated aqueous sodium bisulfate, 10% sodium hydroxide and brine, dried over $MgSO_4$, filtered, concentrated and chromatographed on silica gel (0–2% methanol/chloroform gradient) to give crude 17β-carbo-(2-adamantyl)-oxy-6-t-butylcarboxy-6-azaandrost-4-en-3-one (907 mg, 90%) as a white foam. A portion of this material (896 mg, 1.62 mmol) is treated with trifluoroacetic acid as described in Example 4 above to give after recrystallization from ethyl acetate, 17β-carbo-(2-adamantyl)-oxy-6-azaandrost-4-en-3-one as a crystalline solid: mp>280° C. (decomp.). Anal. Calcd. for $C_{29}H_{41}NO_3 \cdot H_2O$: C, 74.16; H, 9.23; N, 2.98. Found C, 73.96; H, 9.22; N, 2.97.

Example 74

17β-Carbo-(1-adamantyl)-oxy-6-azaandrost-4-en-3-one (Compound 74)

17β-Carbo-(1-adamantyl)-oxy-6-azaandrost-4-en-3-one is prepared as described in Example 73 from 17β-carboxy-6-t-butylcarboxy-6-azaandrost-4-en-3-one and 1-adamantanol to give a pale yellow crystalline solid; m.p. 273°–275° C. Anal. Calcd. for $C_{29}H_{41}NO_3 \cdot H_2O$: C, 74.16; H, 9.23; N, 2.98. Found: C, 74.15; H, 9.23; N, 2.95.

Example 75

17β-N,N-Diethylcarbamoyl-6-azaandrost-2-(α,β)-methyl-4-en-3-one (Compound 75)

A solution of 17β-N,N-diethylcarbamoyl-6-t-butylcarboxy-6-azaandrost-4-en-3-one (1.00 g, 2.12 mmol), [prepared from coupling 17β-carboxy-6-t-butylcarboxy-6-azaandrost-4-en-3-one (Example 3, part F) and diethylamine as described in Example 1, part A], in tetrahydrofuran (10 mL) is treated at −78° C. with lithium diisopropylamide (2 eq. in tetrahydrofuran), warmed slightly by removing the dry-ice acetone bath for 10 min, recooled to −78° C. and treated with excess methyl iodide. The solution is then warmed to room temperature, poured into saturated aqueous $NaHSO_4$, extracted with ethyl acetate (2×50 mL), the extracts washed with saturated aqueous NaCl, dried over $MgSO_4$, concentrated and chromatographed to give 17β-N,N-diethylcarbamoyl-6-t-butylcarboxy-6-azaandrost- 2(α,β)-methyl-4-en-3-one; yield: 582 mg (58%). This material is treated with trifluoroacetic acid as described in Example 4 above to give, after recrystallization from methylene chloride/hexane, 17β-N,N-diethylcarbamoyl-6-azaandrost- 2(α,β)-methyl-4-en-3-one as a pale yellow crystalline solid; m.p. 246°–252° C. (decomp). Anal. Calcd. for $C_{24}H_{38}N_2O_4$: C, 74.57; H, 9.91; N, 7.25. Found: C, 74.31; H, 9.86; N, 7.16.

Example 76

17β-1-(E)-Acrylyl(N,N-diethyl)amide-6-azaandrost-4-en-3-one (Compound 76)

A solution of N,N-diethyl-diethylphosphonoacetamide (108 mg, 0.43 mmol) in tetrahydrofuran (2 mL) at 0° C. is treated with lithium bis(trimethylsilyl)amide (1.0M in tetrahydrofuran, 0.41 mL, 0.41 mmol). After 5 minutes, 17β-formyl-6-t-butylcarboxy- 6-azaandrost-4-en-3-one, (prepared as described in Example 5, part B), (150 mg, 0.37 mmol) in tetrahydrofuran (3 ml) is added and the reaction proceeds for 10 minutes at 0° C. before being allowed to warm to ambient temperature. After 15 minutes, the reaction is quenched with water (0.5 ml), diluted with ethyl acetate (40 ml), washed with saturated aqueous $NaHSO_4$, saturated aqueous NaCl, dried over $MgSO_4$, concentrated and chromatographed on silica gel (0–3% methanol/methylene chloride) to give 17β-1-(E)-acrylyl(N,N-diethyl)amide- 6-t-butylcarboxy-6-azaandrost-4-en-3-one as a, yellow oil; yield: 150 mg (82%); FAB mass spec. $MH^+$ 499. This material is treated with trifluoroacetic acid as described in Example 4 above to give after chromatography and crystallization from acetonitrile, 17β-1-(E)-acrylyl(N,N-diethyl)amide-6-azaandrost-4-en-3-one as an off-white solid; yield: 42 mg (35%); m.p. 232° C. (decomp). Anal. Calcd. for $C_{25}H_{38}N_2O_2 \cdot 7/4H_2O$: C 69.81; H, 9.73; N, 6.51. Found: C, 69.94; H, 9.42; N, 6.49.

Example 77

17β-N,N-Diethylcarbamoyl-6-aza-B-homoandrost-4-en-3-one (Compound 77)

A. To a solution of 17β-N,N-diethylcarbamoyl-androst-4-en-3-one (Rasmusson et al. *J. Med. Chem.*, 27, 1690, (1984); id, 29, 2298 (1986)), (2.00 g, 5.38 mmol) in anhydrous toluene (30 mL) is added anhydrous ethylene glycol (4 mL), p-toluenesulfonic acid (50 mg) and the solution heated at reflux for 5 hrs with azeotropic removal of water. The reaction is then concentrated to about 10 mL, poured into water (60 mL) and extracted with ethyl acetate (2×100 mL). the combined ethyl acetate is washed with saturated aqueous NaCl, dried over $MgSO_4$, and concentrated to a yellow solid. The solid is then triturated with diethyl ether to give a corresponding ketal of formula [(XI), Scheme 2] as a white solid; yield: 1.32 g (59%).

B. The crude product from above is treated with ozone followed by zinc and acetic acid as described in step B, Example 3 above to give a corresponding aldehyde of formula (XII) in 55% yield.

C. The crude aldehyde from above (8.50 g, 19 mmol) is dissolved in THF (160 mL) and treated with lithium tri-t-butoxyaluminum hydride (23 mL, 1,7M, 39 mmol) at −78° C. After 35 minutes the reaction is allowed to warm to 0° C. and quenched with 2N NaOH (12 mL), filtered through Celite, filtrate washed with saturated aqueous NaCl, dried over $MgSO_4$, and concentrated to an oil. Flash chromatography (0–6%, methanol/methylene chloride) gives the compound of formula (XIII) as a clear oil of sufficient purity to carry on to the next step; yield: 6.4 g (75%); FAB mass spec. $MH^+$ 450.2.

D. A solution of the crude alcohol produced in step C (2.07 g, 4.6 mmol) in methylene chloride (40 mL) is treated with triethylamine (0.710 mL, 5.09 mmol) and methanesulfonyl chloride (0.380 mL, 4.91 mmol) and the reaction allowed to stir for 3 hrs. The reaction is then diluted with methylene chloride (25 mL), water added (15 mL), the mixture stirred for 5 minutes, layers separated, washed with saturated aqueous NaCl, dried over $MgSO_4$, and concentrated to an oil. This crude mesylate is then dissolved in dimethylformamide (95 mL) and treated with sodium azide (830 mg, 12.8 mmol) at 80° C. for 1.5 hrs. The reaction is then diluted with water, cooled to room temperature and extracted with diethyl ether (3×70 mL). The combined organics are washed with saturated aqueous NaCl, dried over $MgSO_4$, and concentrated to an oil. Flash chromatography (methylene chloride) gives the corresponding compound of formula (XIV) as a clear oil of sufficient purity to carry on to the next step; yield: 0.840 g (39%).

E. 17β-N,N-Diethylcarbamoyl-6-aza-B-homoandrost-4-en-3-one

The crude azide from part D above (0.840 mg, 1.76 mmol) is dissolved in THF, treated with triphenylphosphine (0.465 g, 1.77 mmol), and heated to reflux for 2 hrs. The reaction is allowed to stir overnight at room temperature, aqueous HCl (4M, 25 mL) and THF (15 mL) added, and the reaction returned to reflux for 2 hrs. The reaction is then concentrated, the aqueous residue made basic with 2N NaOH, extracted with ethyl acetate and 10% methanol in chloroform, the combined extracts washed with saturated aqueous NaCl, dried over $MgSO_4$, and concentrated to give a yellow solid. Flash chromatography (10% methanol/methylene chloride) gives the corresponding compound of formula (I) wherein X is $-CH_2CH_2-$; 17β-N,N-diethylcarbamoyl-6-aza-B-homoandrost-4-en-3-one as a tan solid; yield: 183 mg (26%). Recrystallization from ethyl acetate/diethyl ether gives an analytical sample as a pink solid; m.p. 106°–110° C. Anal. Calcd. for $C_{24}H_{38}N_2O_2 \cdot 1/3H_2O$; C, 73.43; H, 9.93; N, 7.14. Found: C, 73.65; H, 9.88; N, 6.92.

Example 78

Pharmaceutical formulations (A) Transdermal System—For 1000 Patches

| Ingredients | Amount |
| --- | --- |
| Active compound | 400 g |
| Silicone fluid | 450 g |
| Colloidal silicone dioxide | 25 g |

The silicone fluid and active compound are mixed together and the colloidal silicone dioxide is added to increase viscosity. The material is then dosed into a subsequently heat sealed polymeric laminate comprised of the following: polyester release liner, skin contact adhesive composed of silicone or acrylic polymers, a control membrane which is a polyolefin (e.g. polyethylene, polyvinyl acetate or polyurethane), and an impermeable backing membrane made of a polyester multilaminate. The resulting laminated sheet is then cut into 10 sq. cm patches.

(B) Oral Tablet—For 1000 Tablets

| Ingredients | Amount |
| --- | --- |
| Active compound | 50 g |
| Starch | 20 g |
| Magnesium Stearate | 1 g |

The active compound and the starch are granulated with water and dried. Magnesium stearate is added to the dried granules and the mixture is thoroughly blended. The blended mixture is compressed into tablets.

(C) Suppository—For 1000 Suppositories

| Ingredients | Amount |
| --- | --- |
| Active compound | 25 g |
| Theobromine sodium salicylate | 250 g |
| Witepsol S55 | 1725 g |

The inactive ingredients are mixed and melted. The active compound is then distributed in the molten mixture, poured into molds and allowed to cool.

(D) Injection—For 1000 Ampules

| Ingredients | Amount |
| --- | --- |
| Active Compound | 5 g |
| Buffering Agents | q.s. |
| Propylene glycol | 400 mg |
| Water for injection | 600 mL |

The active compound and buffering agents are dissolved in the propylene glycol at about 50° C. The water for injection is then added with stirring and the resulting solution is filtered, filled into ampules, sealed and sterilized by autoclaving.

(E) Capsule—For 1000 Capsules

| Ingredients | Amount |
| --- | --- |
| Active Compound | 50 g |
| Lactose | 450 g |
| Magnesium stearate | 5 g |

The finely ground active compound is mixed with the lactose and stearate and packed into gelatin capsules.

We claim:

1. A pharmaceutical formulation comprising a compound of formula (1):

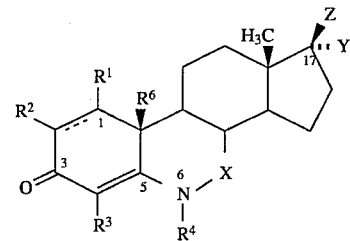

wherein $R^1$ and $R^2$ are,
  i) independently hydrogen or lower alkyl and the bond between the carbons bearing $R^1$ and $R^2$ is a single or a double bond, or
  ii) taken together are a $-CH_2-$ group to form a cyclopropane ring, and the bond between the carbons bearing $R^1$ and $R^2$ is a single bond;

$R^3$ is hydrogen, $-Alk^1-H$ optionally substituted with one or more halogen atoms, lower cycloalkyl, lower cycloalkyl-lower alkyl, halogen,
  $-(Alk^1)_n-CO_2H$,
  $-(Alk^1)_n-CO_2R^7$, $-(Alk^1)_n-Ar^1$, $-(Alk^1)_n-CONR^8R^9$,
  $-(Alk^1)_n-NR^8R^9$,
  $-(Alk^1)_n-S(O)_rR^7$, $-(Alk^1)_n-CN$, $-(Alk^1)-OH$ or
  $-(Alk^1)_n-OR^7$; wherein
    $Alk^1$ is lower alkylene, lower alkenylene or lower alkynylene;
    n is 0 or 1;

r is 0, 1 or 2;

$R^7$ is -Alk$^1$-H, -(Alk$^1$)$_n$-Ar$^1$ or lower cycloalkyl;

$R^8$ and $R^9$ are independently hydrogen, -Alk$^1$-H or lower cycloalkyl;

Ar$^1$ is an aromatic group of 6 to 14 carbons;

$R^4$ is hydrogen, -Alk$^1$-H, lower cycloalkyl, lower cycloalkyl-lower alkyl, -(Alk$^1$)$_n$-S(O)$_r$R$^7$, -(Alk$^1$)$_n$-phthalimidyl, -(Alk$^1$)-CO$_2$H, -(Alk$^1$)-CO$_2$R$^7$, -(Alk$^1$)$_n$-Ar$^1$, -(Alk$^1$)$_n$-CONR$^8$R$^9$, -(Alk$^1$)$_n$-NR$^8$R$^9$, -(Alk$^1$)$_n$-OH or -(Alk$^1$)$_n$-OR$^7$;

X is,

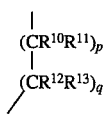

wherein $R^{10}$, $R^{11}$, $R^{12}$ and $R^{13}$ are independently hydrogen or lower alkyl, p and q are independently either 0 or 1;

Y is hydrogen;

Z is -(Alk$^2$)$_n$-COR$^5$, -(Alk$^2$)$_n$-CO$_2$R$^5$, -(Alk$^2$)$_n$-CO-thiopyridinyl or -(Alk$^2$)$_n$-CONR$^{14}$R$^{15}$, wherein Alk$^2$ is (C$_{1-2}$) alkylene, (C$_{2-12}$) alkenylene or (C$_{2-12}$) alkynylene;

$R^5$ is hydrogen, -Alk$^1$-H, lower cycloalkyl or adamantyl;

$R^{14}$ and $R^{15}$ are,
  a) independently, hydrogen, -Alk$^2$-H, lower cycloalkyl, lower alkoxy, adamantyl, -Ar$^1$, benzyl, diphenylmethyl, triphenylmethyl or -(Alk$^1$)$_n$-norbornyl; or
  b) carbon atoms taken together with the linking nitrogen to form a 4 to 8 atom heterocyclic group,

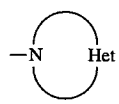

optionally substituted with one or more lower alkyl groups, wherein Het represents —O—, —CH$_2$—, —S(O)$_r$—, —NH— or -N(-Alk$^1$-H);

$R^6$ is hydrogen or methyl;

or a pharmaceutically acceptable salt thereof; in a pharmaceutically acceptable carrier therefor.

2. A composition according to claim 1 wherein the compound of formula (1) is a compound of formula (1A), (1B), (1C) or (1D)

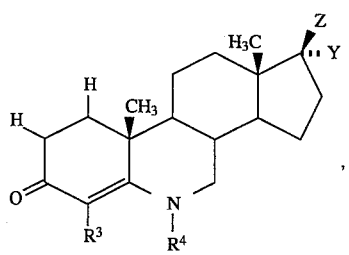

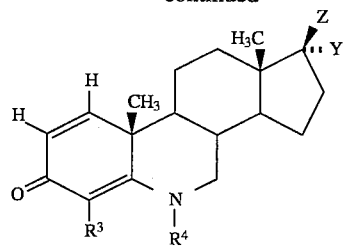

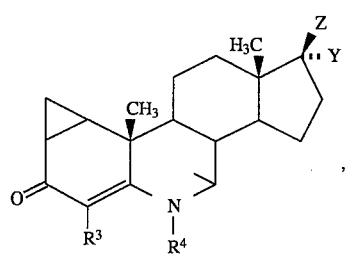

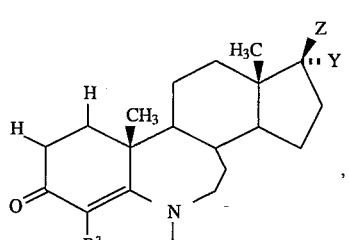

3. A composition according to claim 1 wherein Z in the compound of formula (1) is —COOH, —COOCH$_3$, adamantylcarbamoyl, t-butylcarbamoyl, oxomethylbutyl, methoxymethylcarbamoyl, dimethycarbamoyl, diethylcarbamoyl, di-i-propylcarbamoyl, di-t-butylcarbamoyl, piperazinocarbamoyl, morpholinocarbamoyl, 2-methylpropylcarbamoyl, pyridinylthiocarbonyl, diphenylmethylcarbamoyl, triphenylmethylcarbamoyl, diphenylcarbamoyl, naphthylcarbamoyl, anthracylcarbamoyl, carboadamantytoxy, acrylydiethylamide, exonorbornylmethylcarbamoyl, endonorbornylcarbamoyl, thiomorpholinocarbamoyl or benzylcarbamoyl.

4. A composition according to claim 1 wherein in the compound of formula (1) $R^4$ is hydrogen, methyl, ethyl, propyl, i-propyl, butyl, i-butyl, t-butyl, hexyl, 3-hydroxypropyl, propenyl, methylene-cyclopropyl, benzyl, 2-methoxyethyl, 2-acetic acid, 3-propanoic acid, 4-butanoic acid, 5-pentanoic acid, 6-hexanoic acid, methyl-5-pentanoate, ethyl-6-hexanoate, 3-phthalimidylpropyl or 4-phthalimidylbutyl.

5. A composition according to claim 1 wherein in the compound of formula (1) $R^3$ is hydrogen, methyl, ethyl, cyano, iodo, bromo, chloro or dimethylaminomethyl.

6. A composition according to claim 1 wherein the compound of formula (1) is

17β-N,N-Diethylcarbamoyl-6-azaandrost-4-en-3-one,

17β-N,N-Diethylcarbamoyl-6-methyl-6-azaandrost-4-en-3-one,

17β-N-t-Butylcarbamoyl-6-azaandrost-4-en-3-one,

17β-(2-Pyridinylthiocarbonyl)-6-azaandrost-4-en-3-one,

17β-(1-Oxo-3-methylbutyl)-6-azaandrost-4-en-3-one,

17β-N,N-Diethylcarbamoyl-6-azaandrost-1,4-dien-3-one,

17β-N,N-Diethylcarbamoyl-6-azaandrost-1α,2α-cyclopropyl-4-en-3-one,

17β-N,N-Diethylcarbamoyl-6-azaandrost-4-chloro-4-en-3-one,

17β-N,N-Diethylcarbamoyl-6-azaandrost-4-bromo-4-en-3-one,

17β-N,N-Diethylcarbamoyl-6-azaandrost-4-iodo-4-en-3-one,
17β-N,N-Diethylcarbamoyl-6-azaandrost-4-methyl-4-en-3-one,
17β-N,N-Diethylcarbamoyl-6-azaandrost-4-ethyl-4-en-3-one,
17β-N,N-Diethylcarbamoyl-6-azaandrost-4-cyano-4-en-3-one,
17β-N,N-Diethylcarbamoyl-6-azaandrost-4-dimethylaminomethylene-4-en-3-one,
17β-N,N-Diethylcarbamoyl-6-(3-hydroxypropyl)-6-azaandrost-4-en-3-one,
17β-N-t-Butylcarbamoyl-6-methyl-6-azaandrost-4-en-3-one,
17β-N,N-Diisopropylcarbamoyl-6-azaandrost-4-en-3-one,
17β-N,N-Diisopropylcarbamoyl-6-methyl-6-azaandrost-4-en-3-one,
17β-N-1-Adamantylcarbamoyl-6-azaandrost-4-en-3-one,
17β-N-1-Adamantylcarbamoyl-6-methyl-6-azaandrost-4-en-3-one,
17β-N-Methoxy-N-methylcarbamoyl-6-azaandrost-4-en-3-one,
17β-N-Piperizinocarbamoyl-6-azaandrost-4-en-3-one,
17β-N-Morpholinocarbamoyl-6-azaandrost-4-en-3-one,
17β-Carbomethoxy-6-azaandrost-4-en-3-one,
17β-Carboxy-6-methyl-6-azaandrost-4-en-3-one,
17β-(1-Oxo-3-methylbutyl)-6-methyl-6-azaandrost-4-en-3-one,
17β-N,N-Diethylcarbamoyl-6-methyl-6-azaandrost-1,4-dien-3-one,
17β-N-t-Butylcarbamoyl-6-azaandrosl-1,4-dien-3-one,
17β-N-t-Butylcarbamoyl-6-methyl-6-azaandrost-1,4-dien-3-one,
17β-N-1-Adamantylcarbamoyl-6-azaandrost-1,4-dien-3-one,
17β-N-1-Adamantylcarbamoyl-6-methyl-6-azaandrost-1,4-dien-3-one,
17β-N,N-Diethylcarbamoyl-6-methyl-6-azaandrost-1α,2β-cyclopropyl-4-en-3-one,
17β-N-t-Butylcarbamoyl-6-azaandrost-1α,2α-cyclopropyl-4-en-3-one,
17β-N-t-Butylcarbamoyl-6-methyl-6-azaandrost-1α,2α-cyclopropyl-4-en-3-one,
17β-N,N-Diethylcarbamoyl-6-ethyl-6-azaandrost-4-en-3-one,
17β-N,N-Diethylcarbamoyl-6-propyl-6-azaandrost-4-en-3-one,
17β-N,N-Diethylcarbamoyl-6-butyl-6-azaandrost-4-en-3-one,
17β-N,N-Diethylcarbamoyl-6-hexyl-6-azaandrost-4-en-3-one,
17β-N,N-Diethylcarbamoyl-6-isopropyl-6-azaandrost-4-en-3-one,
17β-N,N-Diethylcarbamoyl-6-isobutyl-6-azaandrost-4-en-3-one,
17β-N,N-Diethylcarbamoyl-6-methylene-cyclopropyl-6-azaandrost,4-en-3-one,
17β-N,N-Diethylcarbamoyl-6-allyl-6-azaandrost-4-en-3-one,
17β-N,N-Diethylcarbamoyl-6-benzyl-6-azaandrost-4-en-3-one,
17β-N,N-Diethylcarbamoyl-6-(2-acetic acid)-6-azaandrost-4-en-3-one,
17β-N,N-Diethylcarbamoyl-6-(3-propanoic acid)-6-azaandrost-4-en-3-one,
17β-N,N-Diethylcarbamoyl-6-(methyl-3-propanoate)-6-azaandrost-4-en-3-one,
17β-N,N-Diethylcarbamoyl-6-(4-butanoic acid)-6-azaandrost-4-en-3-one,
17β-N,N-Diethylcarbamoyl-6-(5-pentanoic acid)-6-azaandrost-4-en-3-one,
17β-N,N-Diethylcarbamoyl-6-(methyl-5-pentanoate)-6-azaandrost-4-en-3-one,
17β-N,N-Diethylcarbamoyl-6-(6-hexanoic acid)-6-azaandrost-4-en-3-one,
17β-N,N-Diethylcarbamoyl-6-(ethyl-6-hexanoate)-6-azaandrost-4-en-3-one,
17β-N,N-Diethylcarbamoyl-6-(3-phthalimidylpropyl)-6-azaandrost-4-en-3-one,
17β-N,N-Diethylcarbamoyl-6-(4-phthalimidylpropyl)-6-azaandrost-4-en-3-one,
17β-N,N-Diethylcarbamoyl-6-(2-methoxyethyl)-6-azaandrost-4-en-3-one,
17β-N-1-Adamantylcarbamoyl-6-azaandrost-4-bromo-4-en-3-one,
17β-N-1-Adamantylcarbamoyl-6-azaandrost-4-methyl-4-en-3-one,
17β-N-1-Adamantylcarbamoyl-6-methyl-6-azaandrost-4-methyl-4-en-3-one,
17β-N-Diphenyimethylcarbamoyl-6-azaandrost-4-en-3-one,
17β-N-Diphenylcarbamoyl-6-azaandrost-4-en-3-one,
17β-N-exo-2-Norbornylmethylcarbamoyl-6-azaandrost-4-en-3-one,
17β-N-endo-2-Norbornylcarbamoyl-6-azaandrost-4-en-3-one,
17β-N-Butylcarbamoyl-6-azaandrost-4-methyl-4-en-3-one,
17β-N-Thiomorpholinocarbamoyl-6-azaandrost-4-en-3-one,
17β-(1-Oxo-3-methylbutyl)-6-azaandrost-4-methyl-4-en-3-one,
17β-N-Benzylcarbamoyl-6-azaandrost-4-en-3-one,
17β-(1-Oxo-3-methylbutyl)-6-azaandrost-4-bromo-4-en-3-one,
17β-N-1-Anthracylcarbamoyl-6-azaandrost-4-en-3-one,
17β-N,N-Diethylcarbamoyl-6-methyl-6-azaandrost-4-methyl-4-en-3-one,
17β-N-t-Butylcarbamoyl-6-methyl-6-azaandrost-4-methyl-4-en-3-one,
17β-N,N-Diethylcarbamoyl-6-azaandrost-4-fluoro-4-en-3-one,
17β-N-Triphenyimethylcarbamoyl-6-azaandrost-4-en-3-one,
17β-N-1-Naphthylcarbamoyl-6-azaandrost-4-en-3-one,
17β-Carbo-(2-adamantyl)-oxy-6-azaandrost-4-en-3-one,
17β-Carbo-(1-adamantyl)-oxy-6-azaandrost-4-en-3-one,
17β-N,N-Diethylcarbamoyl-6-azaandrost-2(α,β)-methyl-4-en-3-one,
17β-1-(E)-Acrylyl(N,N-diethyl)amide-6-azaandrost-4-en-3-one or
17β-N,N,-Diethylcarbamoyl-6-aza-B-homoandrost-4-en-3-one.

7. A method of inhibiting 5α-testosterone reductase enzyme comprising contacting said enzyme with an effective 5α-testosterone inhibitory amount of a composition of claim 1.

8. A method of treating an androgen responsive or mediated disease in a mammal comprising administering to said mammal, an effective androgen responsive or mediated disease amount of a composition of claim 1.

9. A method of claim 8 wherein the androgen responsive or mediated disease is benign prostatic hypertrophy, prostate cancer, acne, male pattern baldness and hirsutism.

10. A pharmaceutical formulation comprising a compound of formula (1E):

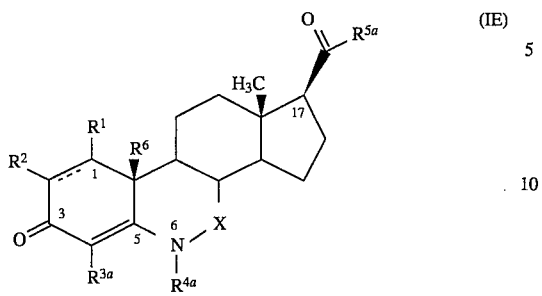

wherein $R^1$ and $R^2$ are
i) independently hydrogen or lower alkyl and the bond between the carbons bearing $R^1$ and $R^2$ is a single or a double bond, or
ii) taken together are a —$CH_2$— group to form a cyclopropane ring, and the bond between the carbons bearing $R^1$ and $R^2$ is a single-bond;

$R^{3a}$ is hydrogen, lower alkyl, lower cycloalkyl, lower cycloalkyl-lower alkyl, lower alkenyl, lower alkynyl, alkanoyl of 2–6 carbons, halogen, —$(CH_2)_n\cdot CO_2R^7$, —$(CH_2)_n\cdot Ar$, —$(CH_2)_n\cdot CONR^8R^9$, —$(CH_2)_n\cdot NR^8R^9$ —$(CH_2)_n\cdot CN$ or —$(CH_2)_n\cdot OR^7$ wherein
$R^7$ is hydrogen, lower alkyl, lower cycloalkyl, lower alkenyl or lower alkynyl;
$R^8$ and $R^9$ are independently hydrogen, lower alkyl, lower cycloalkyl or lower alkenyl;
Ar is an aromatic group of 6 to 12 carbons;
n' is 0 or an integer from 1 to 5;

$R^{4a}$ is hydrogen, lower alkyl, lower cycloalkyl, lower cycloalkyl-lower alkyl, cycloalkyl, lower alkenyl, lower alkynyl, $(CH_2)_m$phthalimidyl, —$(CH_2)_m CO_2R^7$, —$(CH_2)_n\cdot Ar$, —$(CH_2)_m CONR^8R^9$, —$(CH_2)_m NR^8R^9$ or —$(CH_2)_n\cdot OR^7$, wherein
m is an integer from 1 to 5;

X is

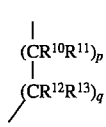

wherein
$R^{10}$, $R^{11}$, $R^{12}$ and $R^{13}$ are independently hydrogen or lower alkyl,
p and q are independently either 0 or 1;

$R^{5a}$ is lower alkyl, lower alkenyl, lower cycloalkyl, lower alkoxy, thiopyridinyl, adamantyl, $NR^{14a}R^{15a}$ or Ar-$NR^{14a}R^{15a}$ wherein
$R^{14a}$ and $R^{15a}$ are
i) idependently, hydrogen or lower alkyl, lower alkenyl, lower alkynyl, lower cycloalkyl, lower alkoxy, adamantyl, aryl, benzyl, diphenylmethyl, norbornyl or ii) taken together with the linking nitrogen to form a 4 to 8 atom heterocyclic group

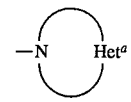

wherein;
$Het^a$ represents O, $CH_2$, NH or N(lower alkyl) optionally substituted with one or more lower alkyl groups;
$R^8$ is hydrogen or methyl; and pharmaceutically acceptable salts thereof in a pharmaceutically acceptable carrier therefor.

11. A pharmaceutical formulation comprising a compound of formula (1G):

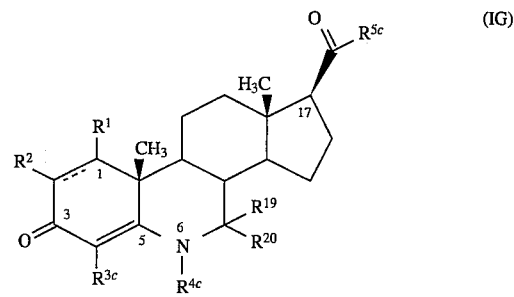

wherein $R^1$ and $R^2$ are
i) independently hydrogen or lower alkyl and the bond between the carbons bearing $R^1$ and $R^2$ is a single or a double bond, or
ii) taken together are a —$CH_2$— group to form a cyclopropane ring, and the bond between the carbons bearing $R^1$ and $R^2$ is a single-bond;

$R^{3c}$ is hydrogen;

$R^{4c}$ is hydrogen, lower alkyl, lower cycloalkyl, lower alkenyl, alkanoyl of 2–6 carbons, —$(CH_2)_m CO_2R^{16}$, —$(CH_2)_m Ar^a$, —$(CH_2)_n\text{'}CONR^{17}R^{18}$, —$(CH_2)_n\text{'}NR^{17}R^{18}$ or —$(CH_2)_n\text{'}OR^{16}$, wherein
$R^{16}$ is hydrogen, lower alkyl or lower alkenyl;
$R^{17}$ and $R^{18}$ are independently hydrogen, lower alkyl, lower cycloalkyl or lower alkenyl;
$Ar^a$ is an aromatic group of 6 to 12 carbons;
n' is 0 or an integer from 1 to 5;
m is an integer from 1 to 5;

$R^{19}$ and $R^{20}$ are independently hydrogen or lower alkyl, or taken together
$R^{19}$ and $R^{20}$ form a carbonyl group(=O);

$R^{5c}$ is lower alkyl, lower alkenyl, lower cycloalkyl, lower alkoxy, or $NR^{21}R^{22}$, wherein
$R^{21}$ and $R^{22}$ are independently hydrogen, lower alkyl or lower alkenyl;

or a pharmaceutically acceptable salt thereof in a pharmaceutically acceptable carrier therefor.

12. A pharmaceutical formulation comprising a compound of formula (1F):

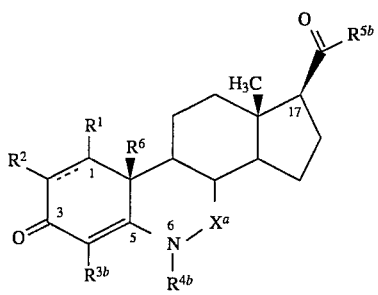

wherein
- $R^1$ and $R^2$ are
  - i) independently hydrogen or lower alkyl and the bond between the carbons bearing $R^1$ and $R^2$ is a single or a double bond, or
  - ii) taken together are a —CH$_2$— group to form a cyclopropane ring, and the bond between the carbons bearing $R^1$ and $R^2$ is a single bond;
- $R^{3b}$ is hydrogen, lower alkyl, lower cycloalkyl, lower cycloalkyl-lower alkyl, lower alkenyl, lower alkynyl, alkanoyl of 2–6 carbons, halogen, —(CH$_2$)$_n$·CO$_2$R$^7$, —(CH$_2$)$_n$·—Ar, —(CH$_2$)$_n$·CONR$^8$R$^9$, —(CH$_2$)$_n$·NR$^8$R$^9$, —(CH$_2$)$_n$·CN or —(CH$_2$)$_n$·OR$^7$ wherein
  - $R^7$ is hydrogen, lower alkyl, lower cycloalkyl, lower alkenyl or lower alkynyl;
  - $R^8$ and $R^9$ are independently hydrogen, lower alkyl, lower cycloalkyl or lower alkenyl;
  - Ar is an aromatic group of 6 to 12 carbons;
  - n' is 0 or an integer from 1 to 5;
- $R^{4b}$ is hydrogen, lower alkyl, lower cycloalkyl, lower cycloalkyl-lower alkyl, lower alkenyl, lower alkynyl, (CH$_2$)$_m$phthalimidyl, —(CH$_2$)'CO$_2$R$^7$, —(CH$_2$)$_n$'Ar, —(CH$_2$)$_m$CONR$^8$R$^9$, —(CH$_2$)$_n$'NR$^8$R$^9$ or —(CH$_2$)$_n$'OR$^7$, wherein
  - m is an integer from 1 to 5;
- $X^a$ is

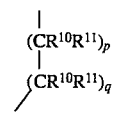

wherein
  - $R^{10}$ and $R^{11}$ are independently hydrogen or lower alkyl,
  - p and q are independently either 0 or 1;
- $R^{5b}$ is lower alkyl, lower alkenyl, lower cycloalkyl, lower alkoxy, thiopyridinyl, adamantyl, NR$^{14b}$R$^{15b}$ or Ar—NR$^{14b}$R$^{15b}$ wherein
  - $R^{14b}$ and $R^{15b}$ are
    - i) independently, hydrogen or lower alkyl, lower alkenyl, lower alkynyl, lower cycloalkyl, lower alkoxy, adamantyl, aryl, benzyl, diphenylmethyl, norbornyl or
    - ii) taken together with the linking nitrogen to form a 4 to 8 atom heterocyclic group
- $R^6$ is hydrogen or methyl; and pharmaceutically acceptable salts thereof in a pharmaceutically acceptable carrier therefor.

* * * * *